(12) United States Patent
Godina

(10) Patent No.: US 11,634,701 B2
(45) Date of Patent: Apr. 25, 2023

(54) METABOLIC PATHWAYS WITH INCREASED CARBON YIELD

(71) Applicant: TOTAL RAFFINAGE CHIMIE, Courbevoie (FR)

(72) Inventor: Alexei Godina, Puteaux (FR)

(73) Assignee: TOTAL RAFFINAGE CHIMIE, Courbevoie (FR)

( * ) Notice: Subject to any disclaimer, the term of this patent is extended or adjusted under 35 U.S.C. 154(b) by 42 days.

(21) Appl. No.: 16/977,168

(22) PCT Filed: Mar. 1, 2019

(86) PCT No.: PCT/EP2019/055194
§ 371 (c)(1),
(2) Date: Sep. 1, 2020

(87) PCT Pub. No.: WO2019/166647
PCT Pub. Date: Sep. 6, 2019

(65) Prior Publication Data
US 2021/0189372 A1 Jun. 24, 2021

(30) Foreign Application Priority Data
Mar. 1, 2018 (EP) .................... 18290018

(51) Int. Cl.
| | |
|---|---|
| C12N 9/88 | (2006.01) |
| C12N 9/16 | (2006.01) |
| C12P 7/52 | (2006.01) |
| C12P 7/54 | (2006.01) |
| C12N 1/21 | (2006.01) |

(52) U.S. Cl.
CPC ............ *C12N 9/88* (2013.01); *C12N 9/16* (2013.01); *C12P 7/52* (2013.01); *C12P 7/54* (2013.01); *C12Y 301/03011* (2013.01); *C12Y 301/03037* (2013.01); *C12Y 401/02009* (2013.01)

(58) Field of Classification Search
None
See application file for complete search history.

(56) References Cited

U.S. PATENT DOCUMENTS

| | | | |
|---|---|---|---|
| 2006/0040365 A1* | 2/2006 | Kozlov ............... | C12P 7/44 435/106 |
| 2013/0089906 A1* | 4/2013 | Beck ............... | C12Y 203/01008 435/254.2 |
| 2014/0295510 A1* | 10/2014 | Koivistoinen ....... | C12N 9/0006 435/254.11 |
| 2016/0060635 A1 | 3/2016 | Liao et al. | |
| 2016/0068831 A1* | 3/2016 | Beck ............... | C12P 5/007 435/34 |

FOREIGN PATENT DOCUMENTS

| | | |
|---|---|---|
| WO | 2014100726 A2 | 6/2014 |
| WO | 2014153036 A1 | 9/2014 |
| WO | 2014169144 A2 | 10/2014 |
| WO | 2015148272 A1 | 10/2015 |

OTHER PUBLICATIONS

Gronenberg et al., Next generation biofuel engineering in prokaryotes, Curr. Opin. Chem. Biol. 17, 2013, 462-71. (Year: 2013).*
Krusemann et al., Artificial pathway emergence in central metabolism from three recursive phosphoketolase reactions, Febs J. 285, 2018, 4367-77. (Year: 2018).*
Miosga et al., Cloning and characterization of the first two genes of the non-oxidative part of the *Saccharomyces cerevisiae* pentose-phosphate pathway, Curr. Genet. 30, 1996, 404-09. (Year: 1996).*
Genbank, Accession No. AAN2477.1, 2014, ncbi.nlm.nih.gov (Year: 2014).*
Genbank, Accession No. AE014295.3, 2014, ncbi.nlm.nih.gov. (Year: 2014).*
Yevenes A et al, "Cloning, expression, purification, cofactor requirements, and steady state kinetics of phosphoketolase-2 from Lactobacillus plantarum", Bioorganic Chemistry, Academic Press Inc., New York, NY, US, vol. 36, No. 3, (2008), pp. 121-127.
Bouke Wim De Jong et al., "Improved production of fatty acid ethyl esters in *Saccharomyces cerevisiae* through up-regulation of the ethanol degradation pathway and expression of the heterologous phosphoketolase pathway", Microbial Cell Factories, (2014), vol. 13, 10 pages.
Bogorad et al., "Synthetic non-oxidative glycolysis enables complete carbon conservation"; Nature, (Oct. 31, 2013), vol. 502, pp. 693-698.
Bogorad et al., "Building carbon-carbon bonds using a biocatalytic methanol condensation cycle"; PNAS, (Nov. 11, 2014), vol. 111, No. 45; pp. 15928-15933.
Leemhuis et al., "Directed Evolution of Enzymes: Library Screening Strategies"; IUBMB Life, (Mar. 2009), vol. 61, pp. 222-228.
Racker, "Fructose-6-phosphate Phosphoketolase from Acetobacter xylinurn: F-6-P+Pi→Acetyl-P+E-4-P+H2O" Methods Enzymol., (1962), vol. 5, pp. 276-280.
Orban; Patterson, "Modification of the phosphoketolase assay for rapid identification of bifidobacteria" J. Microbiol. Methods, (2000), vol. 40, pp. 221-224.

(Continued)

*Primary Examiner* — Robert B Mondesi
*Assistant Examiner* — Todd M Epstein
(74) *Attorney, Agent, or Firm* — Amster, Rothstein & Ebenstein LLP

(57) ABSTRACT

The present invention relates to the conversion of a carbon source into acetyl phosphate with increased carbon yield. In particular, the invention provides metabolically engineered micro-organisms capable of producing acetyl phosphate from a carbon source with increased carbon yield, which micro-organisms have been transformed with at least one exogenous nucleic acid encoding a phosphoketolase having sedoheptulose-7-phosphate phosphoketolase activity and which are further genetically modified to have eliminated transketolase activity. The invention also provides methods for the production of chemicals using said micro-organisms.

15 Claims, 13 Drawing Sheets
Specification includes a Sequence Listing.

(56) References Cited

OTHER PUBLICATIONS

Bergman et al., "Functional expression and evaluation of heterologous phosphoketolases in *Saccharomyces cerevisiae*"; AMB Express, (2016), vol. 6, No. 1, 13 pages.

Schaaff-Gerstenschlager et al., "TKL2, a second transketolase gene of *Saccharomyces cerevisiae*. Cloning, sequence and deletion analysis of the gene"; Eur. J Biochem., (1993), vol. 217, pp. 487-492.

Mans et al., "CRISPR/Cas9: a molecular Swiss army knife for simultaneous introduction of multiple genetic modifications in *Saccharomyces cerevisiae*"; FEMS Yeast Res., (2015), vol. 15, No. 2, pp. 1-15.

Verduyn et al., "Effect of benzoic acid on metabolic fluxes in yeasts: a continuous-culture study on the regulation of respiration and alcoholic fermentation"; Yeast, (1992), vol. 8, pp. 501-517.

Inoue et al., "High efficiency transformation of *Escherichia coli* with plasmids"; Gene, 1990, vol. 96, pp. 23-28.

Lin et al., "Construction and evolution of an *Escherichia coli* strain relying on nonoxidative glycolysis for sugar catabolism"; Proc. Natl. Acad. Sci. U.S.A, (Apr. 3, 2018), vol. 115, No. 14; pp. 3538 3546.

Lee (Ed.) 2009 "Systems Biology and Biotechnology of *Escherichia coli*"; Fig. 9.9 (1 page).

Hsu et al., "DNA targeting specificity of RNA-guided Cas9 nucleases"; Nat Biotechnol. vol. 31, No. 9, Sep. 2013; pp. 827-832.

Doench, Fusi et al., "Optimized sgRNA design to maximize activity and minimize off-target effects of CRISPR-Cas9" Nat Biotechnol. vol. 34, No. 2; Feb. 2016, pp. 184-191.

Jiang et al., "Multigene Editing in the *Escherichia coli* Genome via the CRISPR-Cas9 System"; Appl. Environ. Microbiol.; vol. 81, No. 7, Apr. 2015, pp. 2506-2515.

Mumberg et al., "Yeast vectors for the controlled expression of heterologous proteins in different genetic backgrounds" Gene, vol. 156, 1995, pp. 119-122.

International Search Report issued in Application No. PCT/EP2019/055194, dated Jun. 13, 2019; 5 pages.

\* cited by examiner

FIG. 1
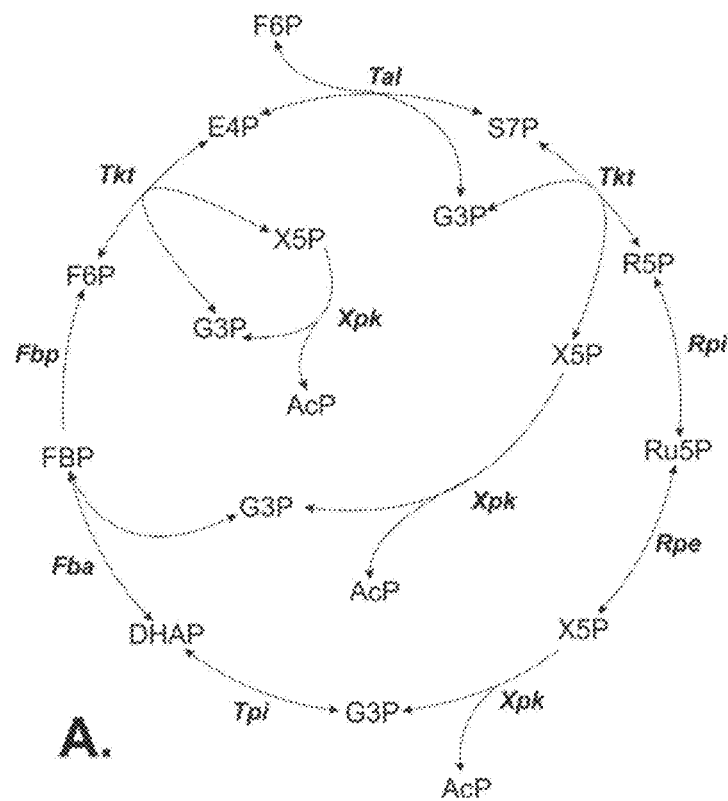
A.
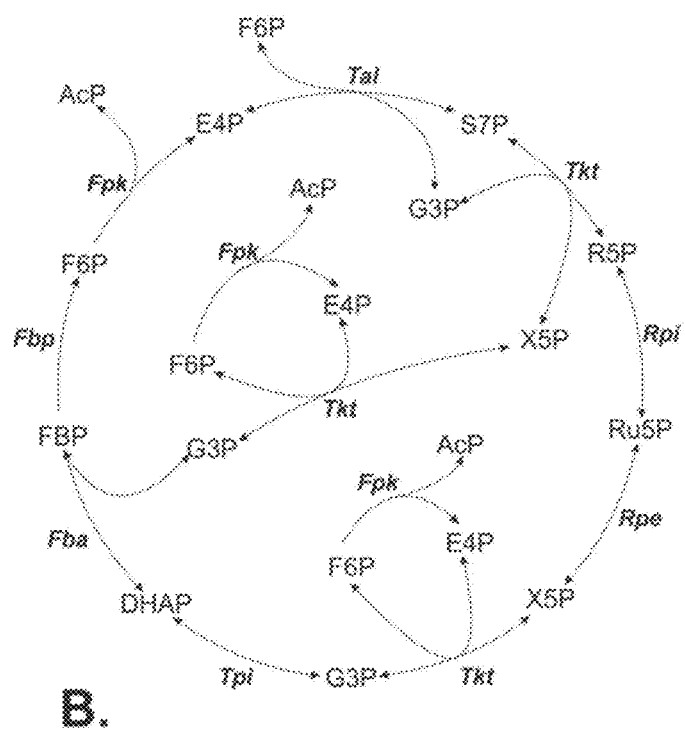
B.

FIG. 8
A
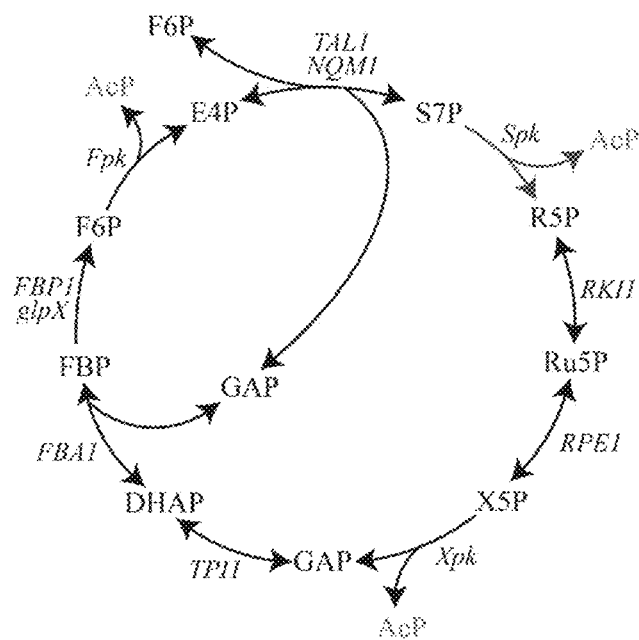
B
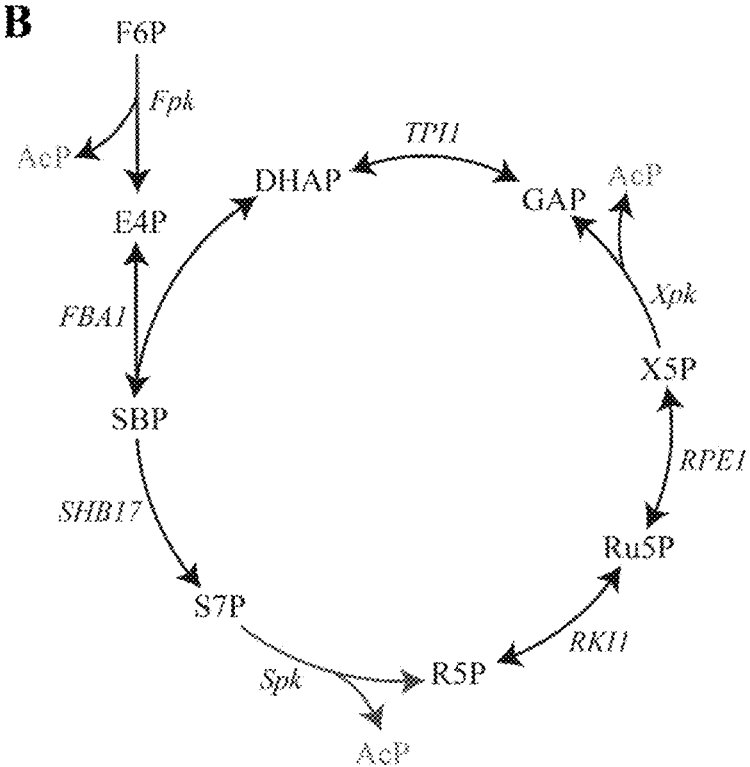

FIG. 9

SEQ ID NO:3

```
ATGACATCCCCTGTAATTGGTACTCCTTGGAAGAAGTTGAACGCCCCAGTCTCAGAAGA
AGCATTGGAAGGTGTTGATAAGTATTGGAGAGTTGCAAATTACTTGTCAATTGGTCAAA
TTTACTTGAGATCAAATCCATTGATGAAAGAACCATTCACTAGAGAAGATGTTAAACAT
AGATTGGTTGGTCATTGGGGTACAACTCCAGGTTTAAATTTCTTGATTGGTCATATTAA
TAGATTCATTGCTGATCATGGTCAAAATACAGTTATTATTATGGGTCCAGGTCATGGTG
GTCCAGCTGGTACTTCACAATCTTACTTGGATGGTACTTATACAGAAACTTTTCCAAAA
ATTACTAAAGATGAAGCAGGTTTGCAAAAATTTTCAGACAATTTTCTTATCCAGGTGG
TATTCCATCTCATTTTGCACCAGAAACACCAGGTTCAATTCATGAAGGTGGTGAATTGG
GTTACGCTTTGTCTCATGCTTATGGTGCAATTATGGATAATCCATCTTTGTTTGTTCCA
GCTATTGTTGGTGACGGTGAAGCTGAAACTGGTCCATTGGCTACTGGTTGGCAATCAAA
TAAGTTGGTTAATCCAAGAACTGATGGTATTGTTTTACCAATTTTGCATTTGAATGGTT
ACAAAATTGCTAATCCAACAATTTTATCAAGAATTTCTGATGAAGAATTGCATGAATTT
TTCCATGGTATGGGTTACGAACCATACGAATTTGTTGCAGGTTTTGATGATGAAGATCA
TATGTCAATTCATAGAAGATTTGCTGAATTATGGGAAACAATTTGGGATGAAATTTGTG
ATATTAAAGCAACAGCTCAAACTGATAATGTTCATAGACCATTTTATCCAATGTTGATT
TTTAGAACACCAAAAGGTTGGACTTGTCCAAAATATATTGATGGTAAAAGACTGAAGG
TTCATGGAGATCACATCAAGTTCCATTAGCATCTGCTAGAGATACTGAAGCACATTTTG
AAGTTTTGAAAAATTGGTTGGAATCTTATAAACCAGAAGAATTGTTTGATGCAAATGGT
GCAGTTAAGATGATGTTTTAGCTTTTATGCCAAAAGGTGAATTGAGAATTGGTGCTAA
TCCAAATGCTAATGGTGGTGTTATTAGAAATGATTTGAAATTACCAAATTTGGAAGATT
ACGAAGTTAAGAAGTTGCAGAATACGGTCATGGTTGGGGTCAATTGGAAGCTACTAGA
ACTTTAGGTGCTTATACTAGAGATATTATTAAAAATAATCCAAGAGATTTTAGAATTTT
TGGTCCAGATGAAACTGCTTCTAATAGATTGCAAGCATCTTATGAAGTTACTAATAAGC
AATGGGATGCTGGTTATATTTCAGATGAAGTTGATGAACATATGCATGTTTCAGGTCAA
GTTGTTGAACAATTGTCAGAACATCAAATGGAAGGTTTCTTGGAAGCATACTTGTTAAC
AGGTAGACATGGTATTTGGTCATCTTATGAATCTTTTGTTCATGTTATTGATTCAATGT
TAAATCAACATGCAAAATGGTTGGAAGCTACAGTTAGAGAAATTCCATGGAGAAAACCA
ATTGCATCTATGAATTTGTTAGTTTCTTCACATGTTTGGAGACAAGATCATAATGGTTT
TTCACATCAAGATCCAGGTGTTACTTCTGTTTTGTTGAATAAGTGTTTTCATAATGATC
ATGTTATTGGTATTTACTTTGCAACTGATGCTAATATGTTGTTAGCTATTGCTGAAAAA
TGTTACAAATCAACTAATAAGATTAATGCAATTATTGCTGGTAAACAACCAGCAGCTAC
TTGGTTAACATTGGATGAAGCTAGAGCAGAATTAGAAAAAGGTGCAGCTGCTTGGGATT
GGGCATCTACTGCTAAAAATAATGATGAAGCTGAAGTTGTTTTAGCAGCAGCTGGTGAC
GTTCCAACTCAAGAAATTATGGCAGCTTCAGATAAATTGAAAGAATTGGGTATTAAATT
CAAAGTTGTTAATGTTGCAGATTTGTTATCATTGCAATCTGCTAAGAAAATGATGAAG
CATTAACTGATGAAGAATTTGCTGATATTTTTACAGCTGATAAACCAGTTTTATTTGCT
TACCATTCTTATGCTCATGATGTTAGAGGTTTGATTTACGATAGACCAAATCATGATAA
TTTTAATGTTCATGGTTATGAAGAAGAAGGTTCAACTACAACTCCATACGATATGGTTA
GAGTTAATAGAATTGATAGATACGAATTGACTGCTGAAGCATTGAGAATGATTGATGCA
GATAAATACGCAGATAAAATTGATGAATTGGAAAAATTCAGAGATGAAGCATTTCAATT
TGCAGTTGATAATGGTTATGATCATCCAGATTATACAGATTGGGTTTACTCAGGTGTAA
ATACCGACAAAAGGGTGCTGTAACCGCTACCGCTGCTACCGCTGGTGACAACGAATAA
```

METABOLIC PATHWAYS WITH INCREASED CARBON YIELD

SEQUENCE LISTING

The instant application contains a Sequence Listing which has been submitted in ASCII format and is hereby incorporated by reference in its entirety. Said ASCII copy, created on Mar. 29, 2022, is named RP18-008_Sequence_listing.txt and is 19,380 bytes in size.

TECHNICAL FIELD

The application generally relates to metabolic engineering of microorganisms. In particular, the application relates to microorganisms that are metabolically engineered to improve the carbon yield of metabolic pathways, more particularly to synthesize acetyl-coenzyme A or products derived therefrom from a suitable carbon source with improved carbon yield.

BACKGROUND

Acetyl-coenzyme A (CoA) is a central metabolite in microorganisms key to amongst others biosynthesis of biofuels and other chemicals such as, without limitation, n-butanol, isobutanol, isopropanol, ethanol, etc.

Acetyl-CoA is generally derived from glycolysis involving the partial oxidation and splitting of external or intracellular sugars to pyruvate, which in turn is decarboxylated to produce acetyl-CoA. The oxidative decarboxylation of pyruvate results in loss of one molecule of $CO_2$ per molecule of pyruvate, thereby limiting the theoretical carbon yield to only two moles of two-carbon ($C_2$) metabolites per mole of hexose. The waste $CO_2$ has a major impact on the overall economy of biosynthetic processes in an industrial context.

The optimization of carbon yield in the metabolic conversion of a carbon source into valuable chemicals lead to the emergence of numerous designed, non-natural metabolic pathways.

For example, a non-oxidative, cyclic pathway, also referred to as Non-Oxidative Glycolytic (NOG) pathway, allows the production of stoichiometric amounts of $C_2$ metabolites from sugar phosphates without carbon loss (Bogorad et al. 2013 Nature 502:693-698; WO2014153036). The NOG pathway exists in various configurations, relying on either fructose-6-phosphate phosphoketolase activity (Fpk) or on xylulose-5-phosphate phosphoketolase activity (Xpk), or on both Fpk and Xpk activities (WO2014/153036). In addition, fructose-1,6-bisphosphate (FBP)-depending NOG pathways exist, and sedoheptulose-1,7-bisphosphate (SBP)-dependent NOG pathways. In an exemplary NOG pathway (FIG. 1B), a sugar phosphate, such as fructose-6-phosphate (F6P), is the start molecule. The fructose-6-phosphate molecule is broken down to an acetyl phosphate molecule (AcP) and an erythrose-4-phosphate molecule (E4P) by the phosphoketolase (Fpk). The erythrose-4-phosphate condensates with another fructose phosphate molecule to yield two pentose-phosphate molecules (xylulose-5-phosphate (X5P) and ribose-5-phosphate (R5P)) after transaldolase (Tal)—transketolase (Tkt)-mediated carbon re-arrangements. The ribose-5-phosphate is isomerised in xylulose-5-phosphate (X5P) by a ribose-5-phosphate isomerase (Rpi) and a ribulose-3-phosphate epimerase (Rpe). Both xylulose phosphate molecules are further split in two molecules of acetyl-phosphate and two molecules of glyceraldehyde-3-phosphate (G3P) which then both undergo carbon rearrangement to regenerate the initially invested fructose 6-phosphate molecule, which can occur in several different ways, for example via a fructose-1,6-bisphosphate-dependent network. The fructose-1,6-bisphosphate-dependent carbon rearrangement network involves ribose-5-phosphatea triose phosphate isomerase (Tpi), a fructose-1,6-bisphosphate aldolase (Fba) and a fructose-1,6-biphosphatase (Fbp).

In general, there exists a need for biosynthetic processes with efficient carbon utilization.

SUMMARY OF THE INVENTION

In certain microorganisms, in particular in *C. acetobutylicum*, metabolic pathways that generate acetyl-CoA and which employ transaldolase-transketolase enzymes, in particular the NOG pathway, are not active, despite the presence of all required enzymes. In particular, the present inventors have found an accumulation of the intermediate sedoheptulose-7-phosphate, which limits these pathways. Without wishing to be bound by theory, it is believed that due to the rapid metabolization of glyceraldehyde-3-phosphate (G3P), which is co-generated with sedoheptulose-7-phosphate (S7P) by the action of Tal and Tkt, S7P is accumulating in these pathways leading to their inefficient use (FIG. 2).

Accordingly, the present inventors have found that increased sedoheptulose-7-phosphate conversion can enhance the carbon fluxes in these organisms via activation of these metabolic pathways, in particular the NOG pathway. In particular, it was found that upon introduction of a sedoheptulose-7-phosphate phosphoketolase (Spk) to convert sedoheptulose-7-phosphate into acetyl-phosphate and ribose-5-phosphate, the accumulation of sedoheptulose-7-phosphate in these pathways, in particular the NOG pathway is reduced or eliminated (FIG. 2), resulting in more efficient pathways. A further advantage is that this is an irreversible reaction and hence constitutes an irreversible driving force for cyclic pathways, such as the NOG pathway, contrary to transketolase (Tkt) and transaldolase (Tal), which are reversible enzymes of which the direction of action is more difficult to control. Furthermore, Spk is a mono-substrate enzyme, i.e. Spk activity requires a single substrate, whereas Tkt and Tal have several substrates, in particular Tkt and Tal catalyze bi-bi reactions (i.e. reactions catalyzed by a single enzyme in which two substrates and two products are involved), further complicating the control of their activity. In addition, the conversion products obtained by splitting sedoheptulose-7-phosphate with Spk are easily metabolized further.

Thus the invention relates to metabolically engineered micro-organisms which have increased conversion of acetyl phosphate from a carbon source compared to a corresponding non-metabolically engineered micro-organism as a result of the introduction of an exogenous gene encoding a phosphoketolase, more particularly a phosphoketolase having sedoheptulose phosphate phosphoketolase activity. In embodiments, the phosphoketolase having sedoheptulose-7-phosphate phosphoketolase activity has also fructose-6-phosphate phosphoketolase activity and/or xylulose-5-phosphate phosphoketolase activity. In particular embodiments, the phosphoketolase having sedoheptulose-7-phosphate phosphoketolase activity is a *Bifidobacterium longum* phosphoketolase or a functional variant thereof such as the phosphoketolase of *Bifidobacterium longum* strain NCC2705.

In particular embodiments, the micro-organism is further selected or engineered to have reduced or eliminated transketolase activity, preferably eliminated transketolase activity. In certain embodiments, elimination of transketolase activity is achieved by deleting the endogenous gene(s) encoding a transketolase (tkt). In particular embodiments, the invention thus provides a metabolically engineered micro-organism capable of increased acetyl phosphate conversion from a carbon source compared to a corresponding non-metabolically engineered micro-organism, wherein the micro-organism comprises at least one exogenous nucleic acid encoding a phosphoketolase having sedoheptulose-7-phosphate phosphoketolase activity, and wherein the micro-organism is further genetically modified to have reduced or eliminated, preferably eliminated, transketolase activity. In certain embodiments, the invention provides a metabolically engineered micro-organism capable of increased acetyl phosphate conversion from a carbon source compared to a corresponding non-metabolically engineered micro-organism, wherein the micro-organism comprises at least one exogenous nucleic acid encoding a phosphoketolase having sedoheptulose-7-phosphate phosphoketolase activity, and a deletion of the endogenous gene(s) encoding a transketolase.

In further embodiments, the micro-organism is further selected or engineered to have eliminated transketolase activity and eliminated transaldolase activity. In certain embodiments, elimination of transketolase activity and transaldolase activity is achieved by deleting the endogenous genes encoding a transketolase (tkt) and a transaldolase (tal). Accordingly, in certain embodiments, a metabolically engineered micro-organism is provided that comprises at least one exogenous nucleic acid encoding a phosphoketolase having sedoheptulose-7-phosphate phosphoketolase activity, a deletion of the endogenous gene(s) encoding a transketolase and a deletion of the endogenous gene(s) encoding a transaldolase.

Surprisingly, micro-organisms wherein the tkt gene(s) is deleted, or both the tkt gene(s) and tal gene(s), are viable e.g. on minimal M9 glucose media. This is unexpected given that transketolase activity is required in micro-organisms for the production of erythrose-4-phosphate, a precursor of aromatic amino acids and vitamins (Lee (Ed.) 2009 "Systems Biology and Biotechnology of *Escherichia coli*", FIG. 9.9).

The micro-organisms of the present invention are of interest for use in different metabolic pathways, more particularly to increase the yield of end-products of said pathways. In particular embodiments, the micro-organisms are further modified to this extent.

In further embodiments, the micro-organisms are further engineered to facilitate a carbon-conserving metabolic pathway that generates acetyl-phosphate from a carbon source such as a metabolic pathway that converts fructose-6-phosphate into 3 molecules acetyl-phosphate, more particularly a metabolic pathway that converts 1 molecule fructose-6-phosphate and 2 molecules phosphate into 3 molecules acetyl-phosphate and 2 molecules water.

In particular embodiments, the micro-organisms are further characterized in that they further comprise or in that they are further engineered to comprise the enzymes of a metabolic pathway that generates acetyl-phosphate and that involves transaldolase-transketolase enzymes. Such metabolic pathways were found to be more efficient in micro-organisms upon genetically modifying the micro-organisms to have reduced or eliminated transketolase activity and optionally reduced or eliminated transaldolase activity, and upon introducing an exogenous nucleic acid encoding a phosphoketolase having sedoheptulose-7-phosphate phosphoketolase activity in these micro-organisms.

In more particular embodiments, the micro-organisms are characterized in that they comprise one or more, preferably all, of an enzyme having fructose-6-phosphoketolase and/or xylulose-5-phosphoketolase activity, a transaldolase, a ribose-5-phosphate isomerase, a ribulose-5-phosphate epimerase, a triose phosphate isomerase, a fructose 1,6-bisphosphate aldolase, and a fructose 1,6-bisphosphatase. Optionally the micro-organisms are engineered to express or overexpress one or more of these enzymes. Accordingly, in particular embodiments, the micro-organism is further engineered to express or overexpress at least one enzyme selected from the group comprising an enzyme having fructose-6-phosphoketolase and/or xylulose-5-phosphoketolase activity, a transaldolase, a ribose-5-phosphate isomerase, a ribulose-5-phosphate epimerase, a triose phosphate isomerase, a fructose 1,6-bisphosphate aldolase, and a fructose 1,6-bisphosphatase, preferably a fructose 1,6-bisphosphatase.

In more particular embodiments, the presence of the phosphoketolase having sedoheptulose-7-phosphate phosphoketolase activity may also increase the efficiency of the methanol condensation cycle. Accordingly, in particular embodiments, the micro-organism comprises an enzyme having fructose-6-phosphoketolase and/or xylulose-5-phosphoketolase activity; a transaldolase; a ribose-5-phosphate isomerase; a ribulose-5-phosphate epimerase; a triose-phosphate isomerase; a fructose-1,6-bisphosphate aldolase or a sedoheptulose-1,7-bisphosphate aldolase; a fructose-1,6 bisphosphatase or a sedoheptulose-1,7-bisphosphatase; a hexulose-6-phosphate synthase; a hexulose-6-phosphate isomerase; and a methanol dehydrogenase; or the micro-organism comprises an enzyme having fructose-6-phosphoketolase and/or xylulose-5-phosphoketolase activity; a transaldolase; a ribose-5-phosphate isomerase; a ribulose-5-phosphate epimerase; a triose-phosphate isomerase; a fructose-1,6-bisphosphate aldolase or a sedoheptulose-1,7-bisphosphate aldolase; a fructose-1,6 bisphosphatase or a sedoheptulose-1,7-bisphosphatase; a dihydroxyacetone synthase; a fructose-6-phosphate aldolase; and a methanol dehydrogenase. In particular embodiments, the micro-organism is further engineered to express or overexpress at least one enzyme selected from the group comprising an enzyme having fructose-6-phosphoketolase and/or xylulose-5-phosphoketolase activity; a transaldolase; a ribose-5-phosphate isomerase; a ribulose-5-phosphate epimerase; a triose-phosphate isomerase; a fructose-1,6-bisphosphate aldolase or a sedoheptulose-1,7-bisphosphate aldolase; a fructose-1,6 bisphosphatase or a sedoheptulose-1,7-bisphosphatase; a hexulose-6-phosphate synthase; a hexulose-6-phosphate isomerase; and a methanol dehydrogenase; or is further engineered to express or overexpress at least one enzyme selected from the group comprising an enzyme having fructose-6-phosphoketolase and/or xylulose-5-phosphoketolase activity; a transaldolase; a ribose-5-phosphate isomerase; a ribulose-5-phosphate epimerase; a triose-phosphate isomerase; a fructose-1,6-bisphosphate aldolase or a sedoheptulose-1,7-bisphosphate aldolase; a fructose-1,6 bisphosphatase or a sedoheptulose-1,7-bisphosphatase; a dihydroxyacetone synthase; a fructose-6-phosphate aldolase; and a methanol dehydrogenase.

The micro-organisms of the present invention are also of interest in new metabolic pathways that allow for stoichiometric conversion of a carbon source to acetyl phosphate such as the GATHCYC pathway. In particular embodiments, the micro-organisms comprise an enzyme having fructose-6-phosphoketolase activity and/or xylulose-5-phosphoketolase activity, a ribose-5-phosphate isomerase; a ribulose-5- phosphate epimerase; a triose-phosphate isomerase; a sedoheptulose-1,7-bisphosphate aldolase; and a sedoheptulose-1,7-bisphosphatase. In further embodiments, the micro-organisms are further engineered to express or overexpress at least one enzyme selected from the group comprising an enzyme having fructose-6-phosphoketolase activity and/or xylulose-5-phosphoketolase activity, a ribose-5-phosphate isomerase; a ribulose-5-phosphate epimerase; a triose-phosphate isomerase; a sedoheptulose-1,7-bisphosphate aldolase; a sedoheptulose-1,7-bisphosphatase, preferably a sedoheptulose-1,7-bisphosphatase.

In particular embodiments, the micro-organisms described herein are further engineered to have reduced or eliminated activity of an enzyme involved in a competing pathway (i.e. a pathway competing with a metabolic pathway that converts fructose-6-phosphate into 3 molecules acetyl-phosphate) such as (lower) glycolysis or the pentose phosphate pathway. Accordingly, in particular embodiments, the micro-organisms are further engineered to have reduced or eliminated activity of one or more of a phosphoglycerate kinase, a phosphofructokinase and a glucose-6-phosphate dehydrogenase.

In particular embodiments, the micro-organism of the invention is a bacterium or a yeast. In particular embodiments, the micro-organism of the invention is selected from the species *E. coli* or *Clostridium acetobutylicum*, or a yeast. In certain embodiments, the micro-organism is a mixotrophic or a methanotrophic micro-organism.

The invention further relates to applications of the micro-organisms described above. Accordingly, the invention further relates to the use of a micro-organism of the invention for the production of a molecule of interest, said molecule of interest being derived from acetyl-CoA. More particularly, the invention provides methods for the production of a molecule of interest which is derived from acetyl-CoA, wherein said method comprises culturing a metabolically engineered micro-organism according to the invention on a suitable carbon source that can be metabolized by said micro-organism. In particular embodiments, said molecules of interest are selected from polyketides, polyhydroxyalcanoates, hydroxyacids (including 3-hydroxypropionate, 3-hydrobutyrate, 3-hydroxyvalerate and 3-hydroxyhexanoate), fatty alcohols, fatty acids, amino acids (glutamic acid, glutamine, aspartate, asparagine, proline, arginine, methionine, threonine, cysteine, succinate, lysine, leucine, isoleucine), acetone, isopropanol, butanol, isobutanol, isobutene, and propene.

BRIEF DESCRIPTION OF THE FIGURES

The teaching of the application is illustrated by the following Figures which are to be considered as illustrative only and do not in any way limit the scope of the claims.

FIG. 8 shows a Sedoheptulose Phosphoketolase-Assisted Non-Oxidative Glycolysis (SPANOG) pathway (A) and a Glycolysis AlTernative High Carbon Yield Cycle (GATH-CYC) pathway (B) in yeast, in particular in S. cerevisae. The native S. cerevisiae genes are in italics and uppercase; non-native genes are in italics. The phosphoketolase reactions (Fpk, Spk, Xpk) are all catalyzed by the B. longum phosphoketolase (Xfspk).

FIG. 9 shows the nucleotide sequence of the phosphoketolase gene from Bifidobacterium longum NCC2705 (SEQ ID NO: 3), codon optimized for S. cerevisiae.

DETAILED DESCRIPTION OF THE INVENTION

Figure 1:
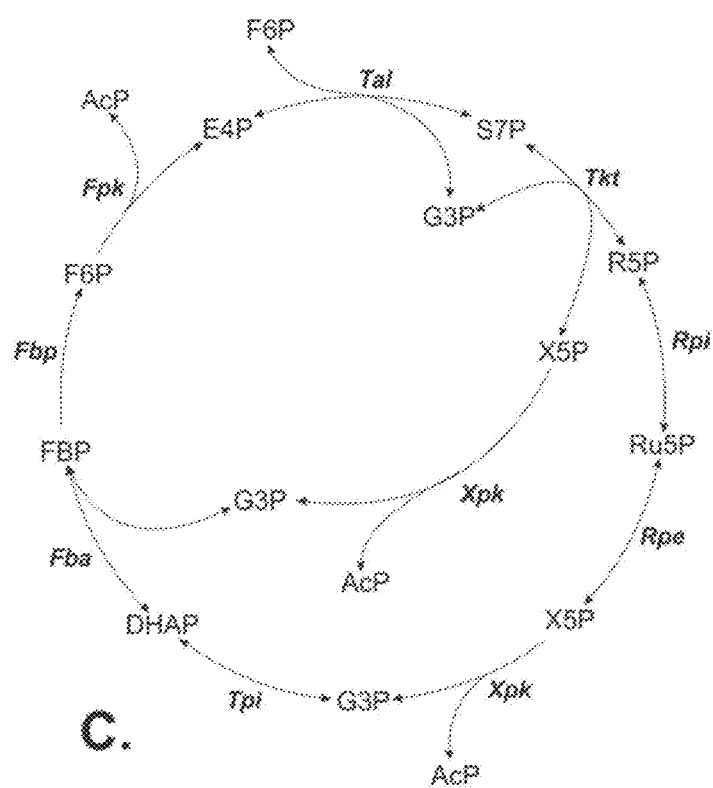
FIG. 1 shows exemplary Non-Oxidative Glycolysis (NOG) pathways for converting a sugar phosphate, in particular fructose-6-phosphate (F6P) to 3 molecules of acetyl phosphate (AcP), involving only Xpk (A) only Fpk (B) or Xpk and Fpk (C). Other abbreviations are: E4P: erythrose-4-phosphate; G3P: glyceraldehyde-3-phosphate; S7P: sedoheptulose-7-phosphate; X5P: xylulose-5-phosphate; DHAP: dihydroxyacetone phosphate; R5P: ribose-5-phosphate; Ru5P: ribulose-5-phosphate; FBP: fructose-1,6-bisphosphate. Fpk: fructose-6-phosphate phosphoketolase; Xpk: xylulose-5-phosphate phosphoketolase; Tal: transaldolase; Tkt: transketolase; Rpi: ribose-5-phosphate isomerase; Rpe: ribulose-3-phosphate epimerase; Tpi: triose phosphate isomerase; Fba: fructose-1,6-bisphosphate aldolase; Fbp: fructose-1,6-biphosphatase.ribose-5-phosphate.
Figure 2:
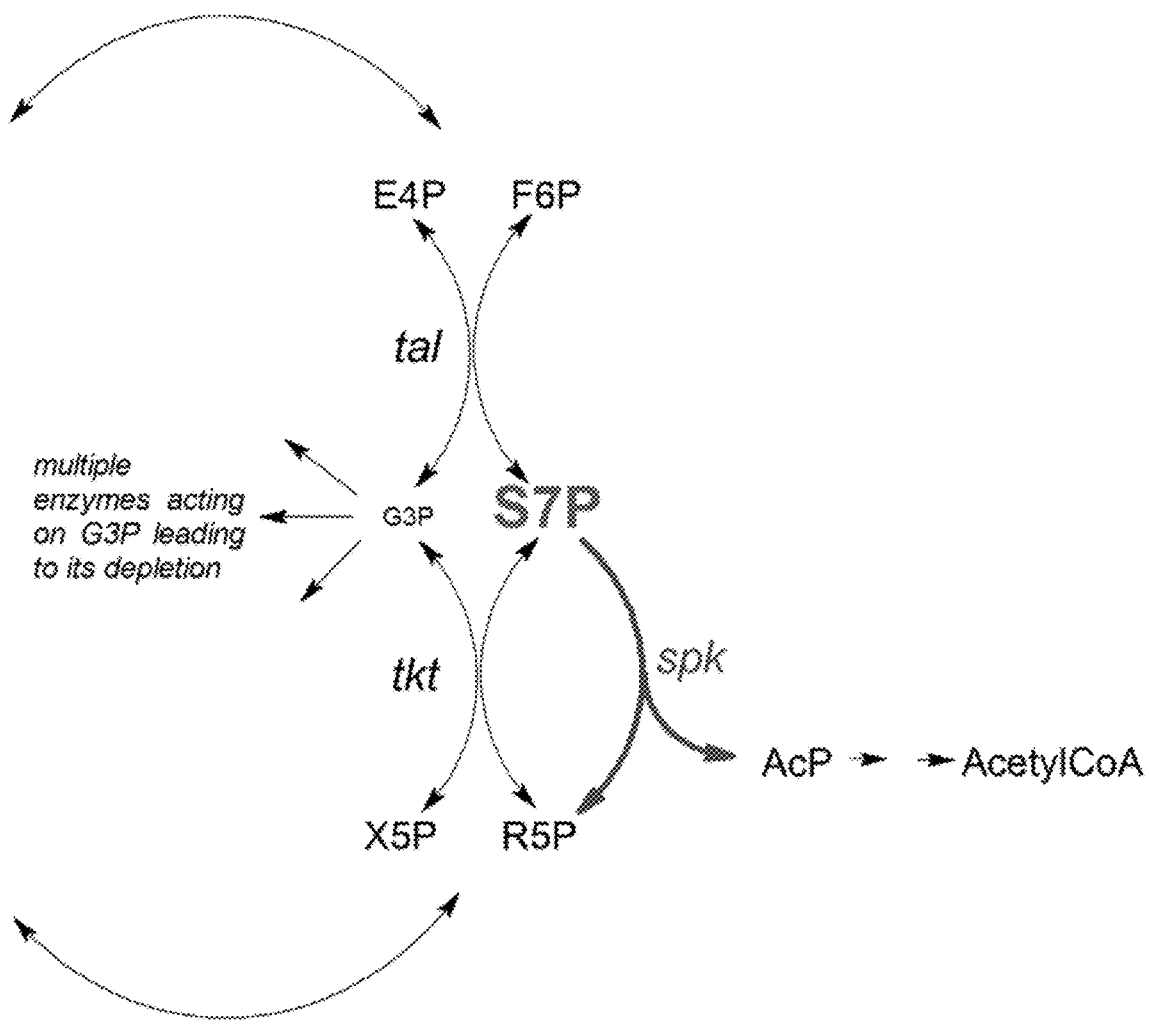
FIG. 2 shows the kinetic bottleneck of metabolic pathways involving transaldolase (Tal) and transketolase (Tkt) enzymes. The action of both enzymes generates sedoheptulose-7-phosphate (S7P) and glyceraldehyde-3-phosphate (G3P), the latter being rapidly depleted by the action of multiple other enzymes, leading to the accumulation of S7P. The enzyme sedoheptulose phosphate phosphoketolase (spk) is capable to eliminate the accumulation of S7P. Other abbreviations are: E4P: erythrose-4-phosphate; F6P: fructose-6-phosphate; X5P: xylulose phosphate; R5P: ribose-5-phosphate; AcP: acetyl-phosphate; AcetylCoA: acetyl-Coenzyme A.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this encompasses also embodiments which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

As used herein, the terms "microbial," "microbial organism" or "micro-organism" are intended to mean any organism that exists as a microscopic cell that is included within the domains of archaea, bacteria or eukaryota. Therefore, the term is intended to encompass prokaryotic or eukaryotic cells or organisms having a microscopic size and includes bacteria, archaea and eubacteria of all species as well as eukaryotic micro-organisms such as fungi, including yeasts, and algae. The term also includes cell cultures of any species that can be cultured for the production of a biochemical.

The terms "genetically engineered" or "genetically modified" or "recombinant" as used herein with reference to a host organism, in particular a micro-organism, or a host cell denote a non-naturally occurring organism or cell, as well as its recombinant progeny, that has at least one genetic alteration not found in a naturally occurring strain of the referenced species, including wild-type strains of the referenced species. Such genetic modification is typically achieved by technical means (i.e. non-naturally) through human intervention and may include, e.g., the introduction of an exogenous nucleic acid and/or the modification of an endogenous nucleic acid. An engineered or modified host organism can also include in the alternative or in addition to the introduction of an exogenous nucleic acid into the host, the disruption, deletion or knocking out of a gene or a polynucleotide. The terms "metabolically engineered" or "metabolically modified" as used herein specifically refer to genetically engineered or modified host cells wherein the genetic alteration induces or modifies or alters a metabolic or biosynthetic pathway.

The terms "biosynthetic pathway" or "metabolic pathway" refer to a set of anabolic or catabolic biochemical reactions for converting one chemical species into another.

The term "exogenous" or "foreign" as used herein is intended to mean that the referenced molecule, in particular nucleic acid, is not naturally present in the host organism or cell. The term "endogenous" or "native" as used herein denotes that the referenced molecule, in particular nucleic acid, is present in the natural, unmodified host organism or cell.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups. Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. The "nucleic acid" can be circular or linear. The term "nucleic acid" as used herein preferably encompasses DNA and RNA, specifically including genomic, hnRNA, pre-mRNA, mRNA, cDNA, recombinant or synthetic nucleic acids, including vectors.

By "encoding" is meant that a nucleic acid sequence or part(s) thereof corresponds, by virtue of the genetic code of an organism in question, to a particular amino acid sequence, e.g., the amino acid sequence of a desired polypeptide or protein, preferably an enzyme. By means of example, nucleic acids "encoding" a particular polypeptide or protein, e.g. an enzyme, may encompass genomic, hnRNA, pre-mRNA, mRNA, cDNA, recombinant or synthetic nucleic acids.

Preferably, a nucleic acid encoding a particular polypeptide or protein, in particular an enzyme, may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide. Hence, the term may be synonymous with "coding sequence" as used in the art.

The present application provides methods and compositions, including metabolically engineered micro-organisms, which ensure an improved carbon yield compared to a pyruvate decarboxylation process for the production of acetyl phosphate. In particular, in the methods and compositions described herein no carbon is lost during the conversion of a carbon source to acetyl phosphate.

In a first aspect, the invention provides metabolically engineered micro-organisms comprising at least one exogenous nucleic acid encoding an enzyme that irreversibly converts sedoheptulose-7-phosphate, in particular a phosphoketolase having sedoheptulose-7-phosphate phosphoketolase activity.

In particular embodiments, the micro-organisms are further genetically modified to have reduced transketolase activity in comparison to micro-organisms that are not genetically modified. In certain embodiments, the micro-organisms are further genetically modified to lack transketolase activity. Thus, provided herein are metabolically engineered micro-organisms comprising at least one exogenous nucleic acid encoding a phosphoketolase having sedoheptulose-7-phosphate phosphoketolase activity, and wherein the micro-organism is further genetically modified to have reduced or eliminated transketolase activity. In embodiments, the micro-organisms having reduced or eliminated transketolase activity described herein may not have reduced or eliminated transaldolase activity. In embodiments, the micro-organisms having reduced or eliminated transketolase activity described herein may have reduced or eliminated activity of one or more other enzymes. In embodiments, the micro-organisms having reduced or eliminated transketolase activity described herein may have reduced or eliminated transaldolase activity.

In particular embodiments, the micro-organisms are further genetically modified to have reduced transketolase activity and reduced transaldolase activity in comparison to micro-organisms that are not genetically modified. In certain embodiments, the micro-organisms are further genetically modified to lack transketolase activity and transaldolase activity. Thus, provided herein are metabolically engineered micro-organisms comprising at least one exogenous nucleic acid encoding a phosphoketolase having sedoheptulose-7-phosphate phosphoketolase activity, and wherein the micro-organism is further genetically modified to have reduced or eliminated transketolase activity and reduced or eliminated transaldolase activity.

As noted before, the introduction of a phosphoketolase having sedoheptulose-7-phosphate phosphoketolase activity was found to eliminate the accumulation of sedoheptulose-7-phosphate in metabolic pathways that generate acetyl-phosphate and which involve transaldolase-transketolase enzymes, resulting in increased acetyl-phosphate production. The reduction or elimination of transketolase activity was shown to have a further beneficial effect on acetyl-phosphate production.

Non-limiting examples of pathways that would benefit from the introduction of an exogenous nucleic acid encoding a phosphoketolase having sedoheptulose-7-phosphate phosphoketolase activity and optionally the reduction of transketolase activity include, without limitation, the Non-Oxidative Glycolytic pathway (Bogorad et al. 2013 Nature 502:693-698; WO2014153036), the Calvin-Benson cycle, and the methanol condensation cycle (also referred to as methanol elongation cycle) (Bogorad et al. 2014 PNAS 111:15928-15933; US20160060635).

Accordingly, in certain embodiments, the invention provides metabolically engineered micro-organisms as described herein that produce acetyl phosphate from a carbon source using a Non-Oxidative Glycolysis pathway. By increasing sedoheptulose-7-phosphate consumption, in particular by the introduction of an exogenous nucleic acid encoding a phosphoketolase having sedoheptulose-7-phosphate phosphoketolase activity, sedoheptulose-7-phosphate accumulation during use of the NOG pathway is reduced or eliminated, and thus kinetic bottleneck effects are reduced or eliminated, resulting in a more efficient NOG pathway. Indeed, sedoheptulose-7-phosphate may inactivate NOG enzymes thereby hampering the NOG pathway. Furthermore, toxic effects in the micro-organism due to sedoheptulose-7-phosphate accumulation are reduced or eliminated. Thus, the phosphoketolase having sedoheptulose-7-phosphate phosphoketolase activity ensures that a NOG pathway is active in the micro-organisms, i.e. that acetyl phosphate is produced from a carbon source using a NOG pathway.

In certain embodiments, the micro-organisms of the invention comprise the required enzymes to convert a carbon source via a sugar phosphate to acetyl phosphate via a NOG pathway. These enzymes may be endogenously present in the micro-organisms described herein, or the enzymes may be introduced into the micro-organisms described herein, or a combination of both is possible. It is further contemplated herein that the micro-organisms described herein may be engineered to overexpress native enzymes.

Different variations of the NOG pathway are possible and any NOG pathway is envisaged herein. Indeed, fructose-1,6-bisphosphate (FBP)-depending pathways exist, involving a transaldolase, a fructose-1,6-bisphosphate aldolase and a fructose-1,6-bisphosphatase, and sedoheptulose-1,7-bisphosphate (SBP)-dependent pathways, which do not involve a transaldolase, but require a sedoheptulose-1,7-bisphosphate aldolase and a sedoheptulose-1,7-bisphosphatase. In addition, for each of these (FBP)-depending pathways and (SBP)-dependent pathways variations exist depending on the phosphoketolase activity: (1) NOG pathways using only a phosphoketolase with fructose-6-phosphoketolase activity (termed Fpk herein), (2) NOG pathways using only a phosphoketolase with xylulose-5-phosphoketolase activity (termed Xpk herein), and (3) NOG pathways using both Fpk and Xpk (termed F/Xpk herein). Non-limiting examples of NOG pathways are described in WO 2014/153036. In particular embodiments, the micro-organisms described herein comprise (a) a polypeptide that catalyzes the production of acetyl-phosphate and erythrose-4-phosphate (E4P) from fructose-6-phosphate (F6P) and/or the production of acetyl-phosphate and glyceraldehyde-3-phosphate (G3P) from xylulose-5-phosphate (X5P); (b) a polypeptide that catalyzes the conversion of fructose-6-phosphate (F6P) and E4P to sedoheptulose-7-phosphate (S7P) and G3P; optionally (c) a polypeptide the catalyzes the conversion of S7P and G3P to ribose-5-phosphate (R5P) and xylulose-5-phosphate (X5P); (d) a polypeptide that catalyzes the conversion of ribose-5-phosphate (R5P) to ribulose-5-phosphate (Ru5P); (e) a polypeptide the catalyzes the conversion of ribulose-5-phosphate (Ru5P) to xylulose-5-phosphate (X5P); (f) a polypeptide that converts glyceraldehyde-3-phosphate to dihydroxyacetone phosphate; (g) a polypeptide that converts dihydroxyacetone phosphate and glyceraldehyde-3-phosphate to fructose-1,6-bisphosphate (FBP) and (h) a polypeptide that converts fructose-1,6-bisphosphate (FBP) to fructose-6-phosphate. In further particular embodiments, the micro-organisms described herein comprise (a) a phosphoketolase (e.g., Fpk, Xpk, or Fpk/Xpk, or homologs thereof); (b) a transaldolase (e.g., Tal, or a homolog thereof); optionally (c) a transketolase (e.g. Tkt, or a homolog thereof); (d) a ribose-5-phosphate isomerase (e.g., Rpi, or a homolog thereof); (e) a ribulose-5-phosphate epimerase (e.g., Rpe, or a homolog thereof); (f) a triose-phosphate isomerase (e.g., Tpi, or a homolog thereof); (g) a fructose-1,6-bisphosphate aldolase (e.g., Fba, or a homolog thereof); and (h) a fructose-1,6 bisphosphatase (e.g., Fbp, or a homolog thereof).

In other embodiments, the micro-organisms of the invention comprise the required enzymes to convert a carbon source, in particular methanol, to acetyl phosphate via a methanol condensation cycle (MCC). Accordingly, in embodiments, the micro-organisms described herein further comprise (a) a polypeptide that catalyzes the production of acetyl-phosphate and erythrose-4-phosphate (E4P) from fructose-6-phosphate (F6P) and/or the production of acetyl-phosphate and glyceraldehyde-3-phosphate (G3P) from xylulose-5-phosphate (X5P); (b) a polypeptide that catalyzes the conversion of fructose-6-phosphate (F6P) and E4P to sedoheptulose-7-phosphate (S7P) and G3P; optionally (c) a polypeptide the catalyzes the conversion of S7P and G3P to ribose-5-phosphate (R5P) and xylulose-5-phosphate (X5P); (d) a polypeptide that catalyzes the conversion of ribose-5-phosphate (R5P) to ribulose-5-phosphate (Ru5P); (e) a polypeptide that catalyzes the conversion of ribulose-5-phosphate (Ru5P) to xylulose-5-phosphate (X5P); (f) a polypeptide that catalyzes the conversion of glyceraldehyde-3-phosphate to dihydroxyacetone phosphate; (g) a polypeptide that catalyzes the conversion of dihydroxyacetone phosphate and glyceraldehyde-3-phosphate (or erythrose-4-phosphate (E4P)) to fructose-1,6-bisphosphate (FBP) (or sedoheptulose-1,7-bisphosphate (SBP)); (h) a polypeptide that catalyzes the conversion of fructose-1,6-bisphosphate (FBP) (or sedoheptulose-1,7-bisphosphate (SBP)) to fructose-6-phosphate (or sedoheptulose-7-phosphate (S7P)); (i) a polypeptide that catalyzes the conversion of formaldehyde (CH2O) and ribulose-5-phosphate (Ru5P) to hexose-6-phosphate (H6P); (j) a polypeptide that catalyzes the conversion of hexose-6-phosphate (H6P) to fructose-6-phosphate (F6P); (k) a polypeptide that catalyzes the conversion of methanol (CH3OH) to formaldehyde (CH2O). In other embodiments, the micro-organisms comprise (a') a polypeptide that catalyzes the production of acetyl-phosphate and erythrose-4-phosphate (E4P) from fructose-6-phosphate (F6P) and/or the production of acetyl-phosphate and glyceraldehyde phosphate (G3P) from xylulose-5-phosphate (X5P); (b') a polypeptide that catalyzes the conversion of fructose-6-phosphate (F6P) and E4P to sedoheptulose-7-phosphate (S7P) and G3P; optionally (c') a polypeptide the catalyzes the conversion of S7P and G3P to ribose phosphate (R5P) and xylulose-5-phosphate (X5P); (d') a polypeptide that catalyzes the conversion of ribose-5-phosphate (R5P) to ribulose-5-phosphate (Ru5P); (e') a polypeptide that catalyzes the conversion of ribulose-5-phosphate (Ru5P) to xylulose-5-phosphate (X5P); (f') a polypeptide that catalyzes the conversion of glyceraldehyde-3-phosphate to dihydroxyacetone phosphate; (g') a polypeptide that catalyzes the conversion of dihydroxyacetone phosphate and glyceraldehyde-3-phosphate (or erythrose-4-phosphate (E4P)) to fructose-1,6-bisphosphate (FBP) (or sedoheptulose-1,7-bisphosphate (SBP)); (h') a polypeptide that catalyzes the conversion of fructose-1,6-bisphosphate (FBP) (or sedoheptulose-1,7-bisphosphate (SBP)) to fructose-6-phosphate (or sedoheptulose-7-phosphate (S7P)); (i') a polypeptide that catalyzes the conversion of formaldehyde (CH2O) and xylulose-5-phosphate (X5P) to glyceraldehyde-3-phosphate (G3P) and glycerone dihydroxyacetone (DHA); (j') a polypeptide that catalyzes the conversion of glyceraldehyde-3-phosphate (G3P) and glycerone dihydroxyacetone (DHA) to fructose-6-phosphate (F6P); (k') a polypeptide that catalyzes the conversion of methanol (CH3OH) to formaldehyde (CH2O). In further particular embodiments, the micro-organisms described herein comprise (a) a phosphoketolase (e.g., Fpk, Xpk, or Fpk/Xpk, or homologs thereof); (b) a transaldolase (e.g., Tal, or a homolog thereof); optionally (c) a transketolase (e.g. Tkt, or a homolog thereof); (d) a ribose-5-phosphate isomerase (e.g., Rpi, or a homolog thereof); (e) a ribulose-5-phosphate epimerase (e.g., Rpe, or a homolog thereof); f) a triose-phosphate isomerase (e.g., Tpi, or a homolog thereof); (g) a fructose-1,6-bisphosphate aldolase or sedoheptulose-1,7-bisphosphate aldolase (e.g., Fba, Sba, or a homolog thereof); and (h) a fructose-1,6 bisphosphatase or sedoheptulose-1,7-bisphosphatase (e.g., Fbp, Sbp, or a homolog thereof); (i) a hexulose-6-phosphate synthase (e.g., Hps, or a homolog thereof); (j) a hexulose-6-phosphate isomerase, (e.g., Phi, or a homolog thereof); (k) methanol dehydrogenase (e.g., Mdh or a homolog thereof). In other further particular embodiments, the micro-organisms described herein comprise (a) a phosphoketolase (e.g., Fpk, Xpk, or Fpk/Xpk, or homologs thereof); (b) a transaldolase (e.g., Tal, or a homolog thereof); optionally (c) a transketolase (e.g. Tkt, or a homolog thereof); (d) a ribose-5-phosphate isomerase (e.g., Rpi, or a homolog thereof); (e) a ribulose-5-phosphate epimerase (e.g., Rpe, or a homolog thereof); f) a triose-phosphate isomerase (e.g., Tpi, or a homolog thereof); (g) a fructose-1,6-bisphosphate aldolase or sedoheptulose-1,7-bisphosphate aldolase (e.g., Fba, Sba, or a homolog thereof); and (h) a fructose-1,6 bisphosphatase or sedoheptulose-1,7-bisphosphatase (e.g., Fbp, Sbp, or a homolog thereof); (i') a dihydroxyacetone synthase (e.g., Das, or a homolog thereof); (j') a fructose phosphate aldolase (e.g., Fsa, or a homolog thereof); (k') methanol dehydrogenase (e.g., Mdh or a homolog thereof).

Figure 7:
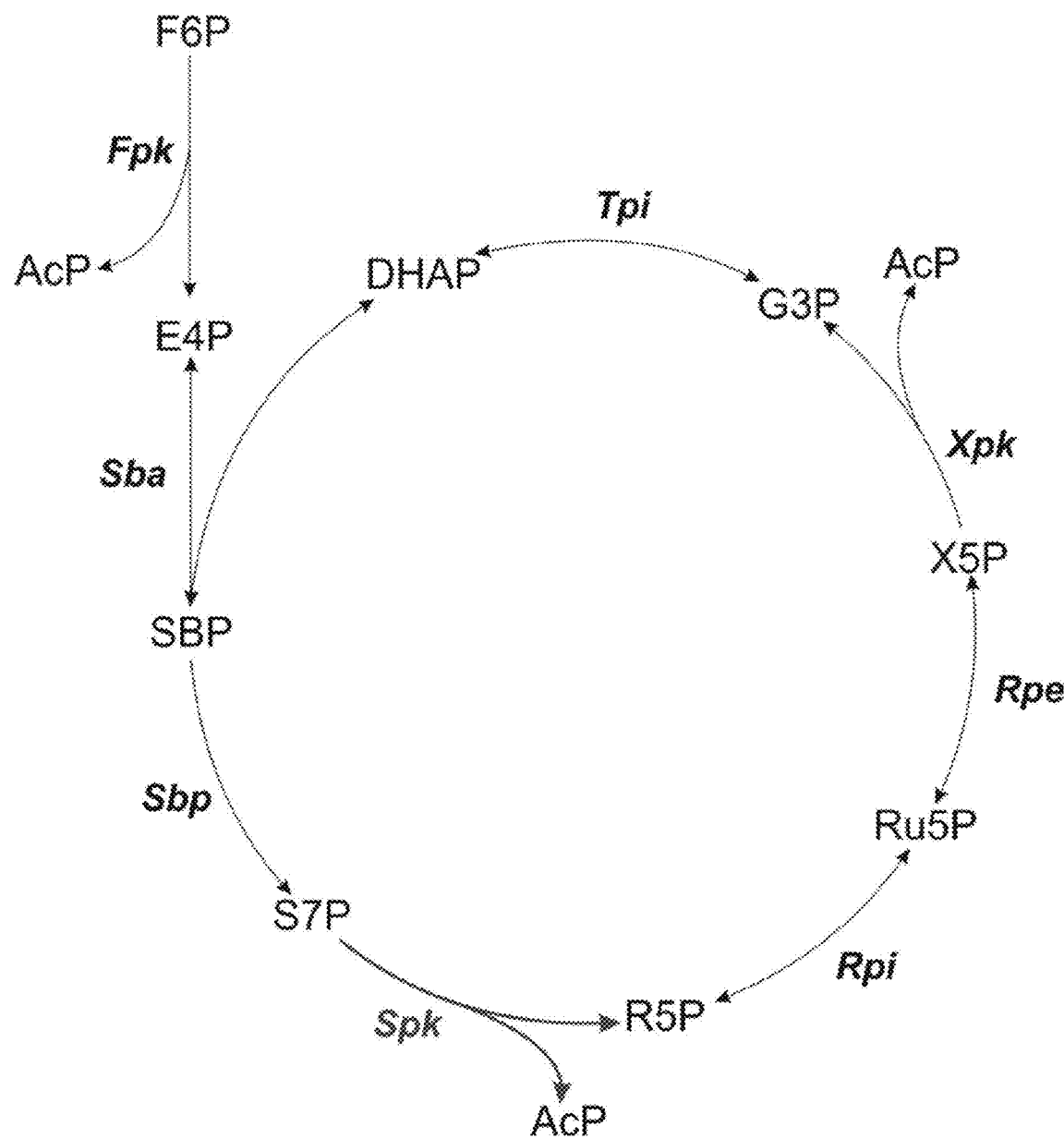
FIG. 7 shows a Glycolysis AlTernative High Carbon Yield Cycle (GATHCYC) for converting a sugar phosphate, in particular fructose 6-phosphate (F6P) to 3 molecules of acetyl phosphate (AcP). Other abbreviations are: E4P: erythrose 4-phosphate; G3P: glyceraldehyde 3-phosphate; S7P: sedoheptulose 7-phosphate; X5P: xylulose 5-phosphate; DHAP: dihydroxyacetone phosphate; R5P: ribose 5-phosphate; Ru5P: ribulose 5-phosphate; SBP: sedoheptulose 1,7-bisphosphate; Spk: sedoheptulose phosphoketolase. Fpk: fructose 6-phosphate phosphoketolase; Xpk: xylulose 5-phosphate phosphoketolase; Rpi: ribose 5-phosphate isomerase; Rpe: ribulose 5-phosphate epimerase; Tpi: triose phosphate isomerase; Sba: sedoheptulose 1,7-bisphosphate aldolase; Sbp: sedoheptulose 1,7-biphosphatase.

In yet other embodiments, the micro-organisms described herein comprise the required enzymes to convert a carbon source via a sugar phosphate, in particular fructose-6-phosphate, to acetyl phosphate via the Glycolysis AlTernative High Carbon Yield Cycle (GATHCYC) pathway (FIG. 7). This GATHCYC pathway is a new carbon-conserving metabolic pathway for stoichiometric conversion of a carbon source to acetyl phosphate, wherein a sugar phosphate, such as fructose-6-phosphate (F6P), is the start molecule. The fructose-6-phosphate molecule is broken down to an acetyl phosphate molecule (AcP) and an erythrose-4-phosphate molecule (E4P) by a phosphoketolase (Fpk). The erythrose-4-phosphate condensates with a di hydroxyacetone phosphate (DHAP) molecule to yield a sedoheptulose-1,7-bisphosphate (SBP) molecule by a sedoheptulose-1,7-bisphosphate aldolase action (Sba). The sedoheptulose-1,7-bisphosphate is dephosphorylated into a sedoheptulose-7-phosphate (S7P) molecule by a sedoheptulose-1,7-bisphosphatase (Sbp). The sedoheptulose-7-phosphate molecule is further split into a molecule of acetyl-phosphate and a ribose-5-phosphate (R5P) molecule by a sedoheptulose-7-phosphate phosphoketolase (Spk). The ribose-5-phosphate is isomerized into xylulose-5-phosphate (X5P) by a ribose-5-phosphate isomerase (Rpi) and a ribulose-3-phosphate epimerase (Rpe). The xylulose-5-phosphate molecule is split into a molecules of acetyl-phosphate and a glyceraldehyde-3-phosphate molecule by xylulose-5-phosphate phosphoketolase (Xpk). The resulting glyceraldehyde-3-phosphate molecule is converted by a triose-phosphate isomerase into dihydroxyacetone phosphate, which condensates with the erythrose-4-phosphate molecule as described above. Advantageously, this GATHCYC pathway has only one enzymatic activity in common with the glycolysis pathway, allowing a glycolysis-independent control over the GATHCYC. The enzymes of this GATHCYC pathway may be endogenously present in the micro-organisms described herein, or the enzymes may be introduced into the micro-organisms described herein, or a combination of both is possible. It is further contemplated herein that the micro-organisms described herein may be engineered to overexpress native enzymes. Accordingly, in particular embodiments, the micro-organisms described herein comprise (a) a polypeptide that catalyzes the production of acetyl-phosphate and erythrose-4-phosphate (E4P) from fructose-6-phosphate (F6P); (b) a polypeptide that catalyzes the condensation of dihydroxyacetone phosphate (DHAP) and erythrose-4-phosphate (E4P) to sedoheptulose-1,7-bisphosphate (SBP); (c) a polypeptide that converts sedoheptulose-1,7-bisphosphate in sedoheptulose-7-phosphate (S7P); (d) a polypeptide that catalyzes the production of acetyl-phosphate and ribose-5-phosphate (R5P) from sedoheptulose-7-phosphate (S7P); (e) a polypeptide that catalyzes the conversion of ribose-5-phosphate (R5P) to ribulose-5-phosphate (Ru5P); (f) a polypeptide the catalyzes the conversion of ribulose-5-phosphate (Ru5P) to xylulose-5-phosphate (X5P); (g) a polypeptide that catalyzes the production of acetyl-phosphate and glyceraldehyde-3-phosphate (G3P) from xylulose-5-phosphate (X5P); (h) a polypeptide that catalyzes the isomerization of dihydroxy-acetone phosphate (DHAP) in glyceraldehyde phosphate (G3P). In further particular embodiments, the micro-organisms described herein comprise (a) a fructose-6-phosphate phosphoketolase (e.g., Fpk or a homolog thereof); (b) a sedoheptulose-1,7-bisphosphate aldolase (e.g., Sba or a homolog thereof); (c) a sedoheptulose-1,7-bisphosphatase (e.g., Sbp or a homolog thereof); (d) sedoheptulose-7-phosphate phosphoketolase (e.g., Spk or a homolog thereof); (e) a ribose-5-phosphate isomerase (e.g., Rpi or a homolog thereof); (f) a ribulose-5-phosphate epimerase (e.g., Rpe or a homolog thereof); (g) a xylulose-5-phosphate phosphoketolase (e.g., Xpk or a homolog thereof); (h) a triose-phosphate isomerase (e.g., Tpi or a homolog thereof). As detailed below, in certain embodiments, the micro-organisms described herein comprise (a') an enzyme having fructose-6-phosphate phosphoketolase activity, sedoheptulose-7-phosphate phosphoketolase activity and xylulose-5-phosphate phosphoketolase activity; (b') a sedoheptulose-1,7-bisphosphate aldolase (e.g., Sba, or a homolog thereof); (c') a sedoheptulose-1,7-bisphosphatase (e.g., Sbp or a homolog thereof); (d') a ribose-5-phosphate isomerase (e.g., Rpi, or a homolog thereof); (e') a ribulose-5-phosphate epimerase (e.g., Rpe, or a homolog thereof); and (f') a triose-phosphate isomerase (e.g., Tpi, or a homolog thereof).

The application provides different ways in which micro-organisms can be genetically engineered to ensure the irreversible conversion of sedoheptulose-7-phosphate. It should be recognized however that reversible conversion of sedoheptulose-7-phosphate may occur in addition to said irreversible conversion.

In preferred embodiments, the micro-organisms described herein comprise an exogenous nucleic acid encoding a phosphoketolase having sedoheptulose-7-phosphate phosphoketolase activity (Spk). With "sedoheptulose-7-phosphate phosphoketolase activity" or "Spk activity" is meant herein the capability of catalyzing the formation of ribose-5-phosphate and acetyl-phosphate from sedoheptulose-7-phosphate. It is recognized however that an enzyme, in particular a phosphoketolase, in addition to said Spk activity, may have other enzyme activities, such as fructose-6-phosphate phosphoketolase activity or Fpk activity (i.e. being capable of catalyzing the formation of acetyl-phosphate and erythrose-4-phosphate from fructose-6-phosphate), and/or xylulose-5-phosphate phosphoketolase activity or Xpk activity (i.e. being capable of catalyzing the formation of acetyl-phosphate and glyceraldehyde-3-phosphate from xylulose-5-phosphate).

In particular embodiments, the phosphoketolase having sedoheptulose-7-phosphate phosphoketolase activity (Spk) is a phosphoketolase from *Bifidobacterium longum*, such as the phospoketolase having the amino acid sequence of SEQ ID NO: 1 (MTSPVIGTPWKKLNAPVSEEALEGVDKY-WRVANYLSIGQIYLRSNPLMKEPFTREDVKHRLVG HWGTTPGLNFLIGHINRFIADHGQNTVIIMGPGH-GGPAGTSQSYLDGTYTETFPKITKDEAGLQ KFFRQF-SYPGGIPSHFAPETPGSIHEGGELGYALSHAYGAIM DNPSLFVPAIVGDGEAETGPLA TGWQSNKLVNPRTD-GIVLPILHLNGYKIANPTILSRISDEELHEFFHGMGYE-PYEFVAGFDDEDH MSIHRRFAELWETIWDEICDI-KAAAQTDNVHRPFYPMLIFRTPKGWTCPKYIDGKK-TEGSWRAH QVPLASARDTEAHFEVLKNWLESYKP-EELFDANGAVKDDVLAFMPKGELRIGANPNANGG-VIR DDLKLPNLEDYEVKEVAEYGHGWGQLE-ATRRLGVYTRDIIKNNPRDFRIFGPDETASNRLQAS YEVTNKQWDAGYISDEVDEHMHVSGQVVE-QLSEHQMEGFLEAYLLTGRHGIWSSYESFVHVI DSMLNQHAKWLEATVREIPWRKPIASMNLL-VSSHVWRQDHNGFSHQDPGVTSVLLNKCFHND HVIGIYFATDANMLLAIAEKCYKSTNKINAI-IAGKQPAATWLTLDEARAELEKGAAAWDWASTAK NNDEAEVVLAAAGDVPTQEIMAASDKLKEL-GVKFKVVNVADLLSLQSAKENDEALTDEEFADIF TADKPVLFAYHSYAHDVRGLIYDRPNHDNFNVHGY-EEEGSTTTPYDMVRVNRIDRYELTAEAL RMIDADKY-ADKIDELEKFRDEAFQFAVDKGYDHPDYTDWV-YSGVNTDKKGAVTATAATAGDN E, also available under NCBI Protein Accession. Version WP_013140548.1) or the phosphoketolase of *Bifidobacterium longum* strain NCC 2705, which has the amino acid sequence of SEQ ID NO: 2 (M T S P V I G T P W K K L N A P V S E E A L E G V D K Y W R V A N Y L S I G Q I Y L R S N P L M K E P F T R E D V K H R L V G H W G T T P G L N F L I G H I N R F I A D H G Q N T V I I M G P G H G G P A G T S Q S Y L D G T Y T E T F P K I T K D E A G L Q K FFRQFSYPGGIPSHFAPETPGSIHEGG
ELGYALSHAYGAIMDNPSLFVPAIVG
DGEAETGPLATGWQSNKLVNPRTDG
IVLPILHLNGYKIANPTILSRISDEEL
HEFFHGMGYEPYEFVAGFDDEDHMS
IHRRFAELWETIWDEICDIKATAQTD
NVHRPFYPMLIFRTPKGWTCPKYIDG
KKTEGSWRSHQVPLASARDTEAHFE
VLKNWLESYKPEELFDANGAVKDDV
LAFMPKGELRIGANPNANGGVIRNDL
KLPNLEDYEVKEVAEYGHGWGQLEA
TRTLGAYTRDIIKNNPRDFRIFGPDE
TASNRLQASYEVTNKQWDAGYISDE
VDEHMHVSGQVVEQLSEHQMEGFLE
AYLLTGRHGIWSSYESFVHVIDSMLN
QHAKWLEATVREIPWRKPIASMNLLV
SSHVWRQDHNGFSHQDPGVTSVLLN
KCFHNDHVIGIYFATDANMLLAIAEK
CYKSTNKINAIIAGKQPAATWLTLDE
ARAELEKGAAAWDWASTAKNNDEAE
VVLAAAGDVPTQEIMAASDKLKELGI
KFKVVNVADLLSLQSAKENDEALTD
EEFADIFTADKPVLFAYHSYAHDVRG
LIYDRPNHDNFNVHGYEEEGSTTTPY
DMVRVNRIDRYELTAEALRMIDADK
YADKIDELEKFRDEAFQFAVDNGYD
HPDYTDWVYSGVNTDKKGAVTATAA
TAGDNE, also available at GenBank under Accession No. AAN24771.1).

Also contemplated herein are (functional) variants of the *Bifidobacterium longum* phosphoketolases described herein. The term "variant", when used in connection to a protein, such as an enzyme, for example as in "a variant of protein X", refers to a protein, such as an enzyme, that is altered in its sequence compared to protein X, but that retains the activity of protein X, such as the enzymatic activity as detailed above (i.e. a functional variant).

These variants may have at least about 99%, 98%, 97%, 96%, 95%, 95%, 93%, 92%, 91%, 90%, 89%, 88%, 87%, 86%, 85%, 80%, 75%, 70%, or 65% sequence identity to the amino acid sequence of SEQ ID NO: 1 or SEQ ID NO: 2, preferably calculated over the entire length of the sequence. The sequence changes may be naturally occurring, for example, due to the degeneracy of the genetic code, or may be introduced artificially, for example by targeted mutagenesis of the respective sequence. Such techniques are well known to the skilled person. In particular embodiments, the functional variant is a non-natural (or synthetic) variant. In particular embodiments, the functional variant is a homolog. The term "homolog" as used herein in connection to a protein, such as an enzyme, for example as in "a homolog of protein X" refers to the fact that the protein differs from protein X in its sequence, but that retains the activity or protein X, such as the enzymatic activity as detailed above, and originates from another species, i.e. is a naturally occurring sequence. A homolog of protein X can be identified by the skilled person by pairwise search methods such as BLAST and checking of the corresponding activity.

In particular embodiments, the phosphoketolase having Spk activity is a synthetic enzyme. As used herein, a "synthetic enzyme" refers to a protein that does not exist in nature (i.e. non-naturally occurring). Synthetic enzymes can be derived from naturally occurring enzymes e.g. by introducing mutations. The synthetic phosphoketolases having Spk activity envisaged herein may be derived from known phosphoketolases. Synthetic phosphoketolases having Spk activity may be obtained by using a survival-based selection system for Spk activity directed evolution in a suitable host cell, e.g. *E. coli*, that is unable to grow on glucose or sedoheptulose in the absence of an enzyme having Spk activity, e.g. due to the knockout of one or more enzymes involved in glycolysis or other vital pathways. Briefly, a mutant DNA library is generated from known phosphoketolases, cloned into an expression vector and transformed in a host cell, which transformed host cell is grown on sedoheptulose. Host cells that survive on glucose or sedoheptulose are selected as having Spk activity. Other strategies for generating synthetic enzymes having Spk activity are described in Leemhuis et al. (2009 IUBMB Life. 61:222-8).

Figure 3:
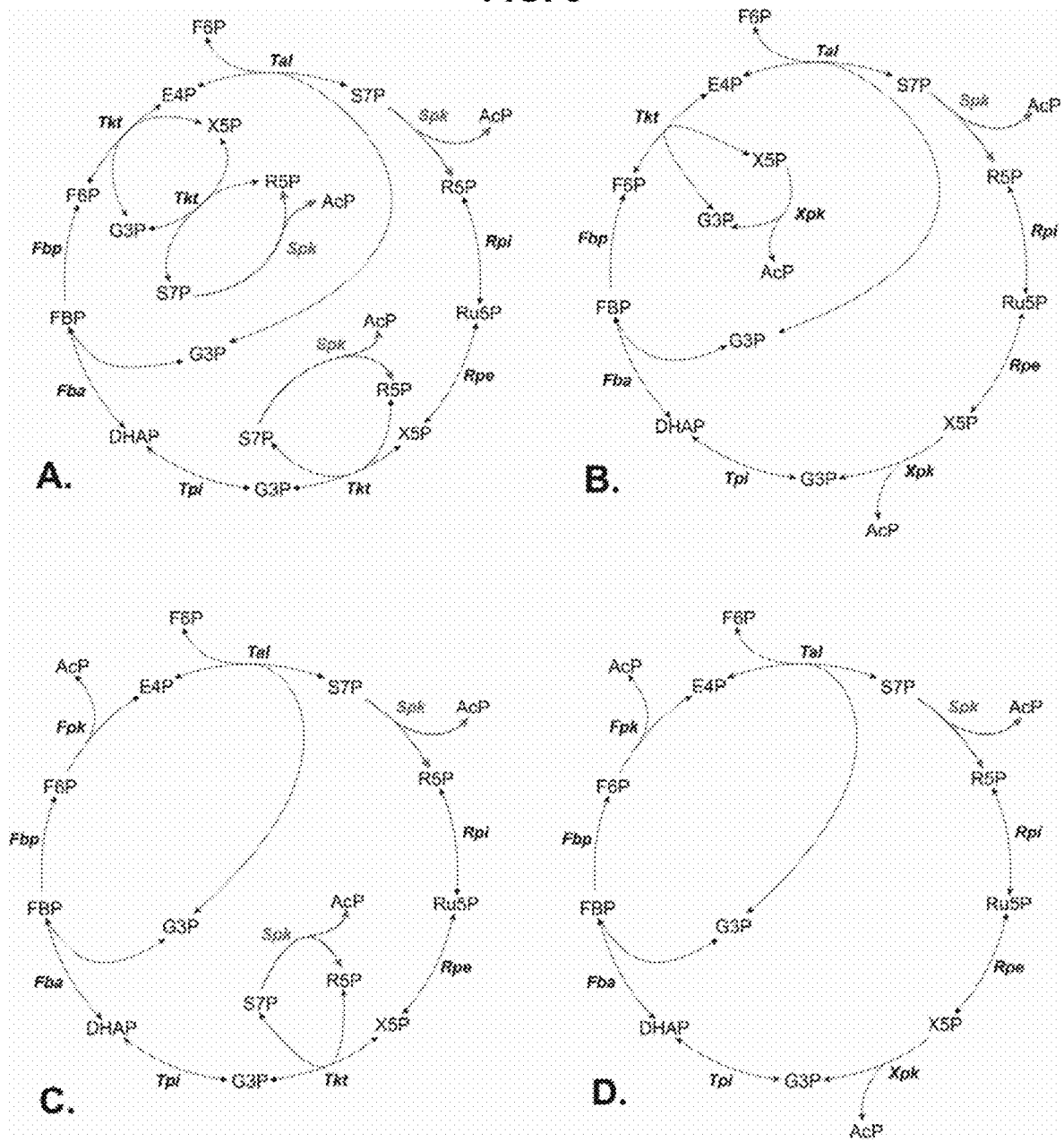
FIG. 3 shows a Sedoheptulose Phosphoketolase-Assisted Non-Oxidative Glycolysis (SPANOG) pathway for converting a sugar phosphate, in particular fructose-6-phosphate (F6P) to 3 molecules of acetyl-phosphate (AcP) involving only Spk (A), Xpk and Spk (B), Fpk and Spk (C), or Xpk, Fpk and Spk (D). Other abbreviations are: E4P: erythrose-4-phosphate; G3P: glyceraldehyde-3-phosphate; S7P: sedoheptulose-7-phosphate; X5P: xylulose-5-phosphate; DHAP: dihydroxyacetone-phosphate; R5P: ribose-5-phosphate; Ru5P: ribulose-5-phosphate; FBP: fructose-1,6-bisphosphate; Spk: sedoheptulose-7-phosphate phosphoketolase; Fpk: fructose-6-phosphate phosphoketolase; Xpk: xylulose-5-phosphate phosphoketolase; Tal: transaldolase; Tkt: transketolase; Rpi: ribose-5-phosphate isomerase; Rpe: ribulose-3-phosphate epimerase; Tpi: triose-phosphate isomerase; Fba: fructose-1,6-bisphosphate aldolase; Fbp: fructose-1,6-biphosphatase.
Figure 4:
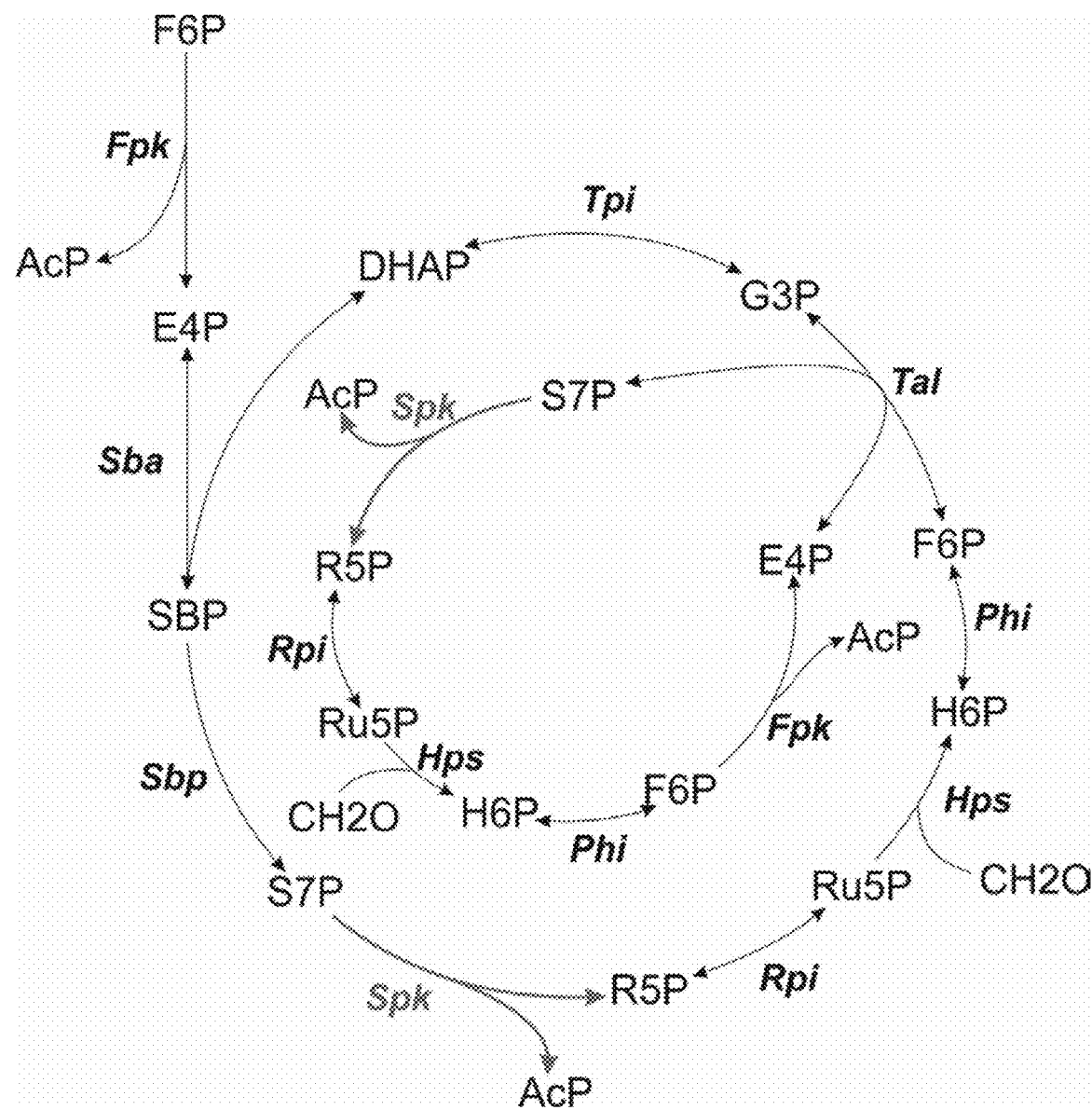
FIG. 4 shows a part of the Sedoheptulose Phosphoketolase-Assisted Methanol Condensation Cycle (SPAMCC), in particular the co-condensation of two molecules of methanol-derived formaldehyde molecules (CH2O) and one molecule of fructose-6-phosphate (F6P) to 4 molecules of acetyl phosphate (AcP). Other abbreviations are: E4P: erythrose-4-phosphate; G3P: glyceraldehyde-3-phosphate; S7P: sedoheptulose-7-phosphate; DHAP: dihydroxyacetone-phosphate; R5P: ribose-5-phosphate; Ru5P: ribulose-5-phosphate; SBP: sedoheptulose-1,7-bisphosphate; H6P: phosphohexulose; Spk: sedoheptulose-7-phosphate phosphoketolase. Fpk: fructose-6-phosphate phosphoketolase; Xpk: xylulose 5-phosphate phosphoketolase; Rpi: ribose-5-phosphate isomerase; Rpe: ribulose-3-phosphate epimerase; Tpi: triose-phosphate isomerase; Sba: sedoheptulose-1,7-bisphosphate aldolase; Sbp: sedoheptulose-1,7-biphosphatase; Hps: H6P synthase; Phi: phosphohexulose isomerase.

The expression or overexpression of a sedoheptulose-7-phosphate phosphoketolase in the micro-organisms described herein is particularly advantageous in that it can irreversibly push the NOG pathway and methanol condensation cycle, resulting in a more efficient NOG pathway/MCC (termed herein sedoheptulose phosphoketolase-assisted non-oxidative glycolytic (SPANOG) pathway and sedoheptulose phosphoketolase-assisted methanol condensation cycle (SPAMCC)). In the SPANOG pathway, the input molecule fructose-6-phosphate and an erythrose-4-phosphate molecule are converted into sedoheptulose-7-phosphate and glyceraldehyde-3-phosphate by a transaldolase similar to known NOG pathways, or the sedoheptulose-7-phosphate is generated from the condensation of erythrose-4-phosphate and dihydroxyacetone phosphate into sedoheptulose-1,7-bisphosphate by sedoheptulose-1,7-bisphosphate aldolase (Sba) followed by sedoheptulose-1,7-bisphosphatase mediated dephosphorylation (for (SBP)-dependent pathways, which do not involve a transaldolase), but then sedoheptulose-7-phosphate is irreversibly converted into ribose-5-phosphate and an acetyl phosphate molecule by an enzyme having Spk activity instead of being converted by a transketolase, and the glyceraldehyde-3-phosphate is directly converted into dihydroxyacetone phosphate by a triose-phosphate isomerase (FIG. 3). In the sedoheptulose phosphoketolase-assisted methanol condensation cycle, the input molecule methanol is reduced to formaldehyde (CH2O) by methanol dehydrogenase; then, the formaldehyde condensates with a ribulose-5-phosphate (Ru5P) (via hexulose-6-phosphate synthase (Hps) and hexulose-6-phosphate isomerase (Phi); or via dihydroxyacetone synthase and fructose-6-phosphate aldolase) to yield a fructose-6-phosphate (F6P); and the fructose-6-phosphate (or a new input molecule fructose-6-phosphate) and an erythrose-4-phosphate (E4P) molecule are converted into sedoheptulose-7-phosphate (S7P) and glyceraldehyde-3-phosphate (G3P) by a transaldolase (Tal) or the sedoheptulose-7-phosphate is generated from the condensation of ab erythrose-4-phosphate and a dihydroxyacetone phosphate into sedoheptulose-1,7-bisphosphate by sedoheptulose-1,7-bisphosphate aldolase (Sba) followed by sedoheptulose-1,7-bisphosphatase mediated dephosphorylation, but then, contrary to known MCC pathways, sedoheptulose-7-phosphate is irreversibly converted into ribose-5-phosphate and acetyl phosphate by an enzyme having Spk activity instead of being converted by a transketolase, and the glyceraldehyde-3-phosphate is directly converted into dihydroxyacetone phosphate by a triose-phosphate isomerase (FIG. 4). In contrast, transketolase (Tkt) and transaldolase (Tal) that are involved in the NOG pathway and MCC are reversible enzymes of which the direction of action is more difficult to control, and these enzymes have different substrates, further complicating the control of their activity.

In further embodiments, the micro-organisms described herein are further genetically modified to have reduced transketolase activity. In certain embodiments, the micro-organisms are genetically modified to lack transketolase activity. In embodiments, the micro-organisms having reduced or eliminated transketolase activity described herein do not have reduced or eliminated transaldolase activity. In embodiments, the micro-organisms having reduced or eliminated transketolase activity described herein have reduced or eliminated activity of one or more other enzymes. In embodiments, the micro-organisms having reduced or eliminated transketolase activity described herein have reduced or eliminated transaldolase activity.

In further embodiments, the micro-organisms described herein are further genetically modified to have reduced transketolase activity and reduced transaldolase activity. In certain embodiments, the micro-organisms are genetically modified to lack transketolase activity and transaldolase activity.

The expressions "reduced transketolase activity" and "reduced transaldolase activity" within the context of the present invention encompasses "eliminated transketolase activity" and "eliminated transaldolase activity", respectively and mean a reduction in the expression of endogenous genes (including knock-out of expression), which encode the transketolase or the transaldolase, and/or a reduction in the quantity of transketolase or transaldolase protein in the micro-organisms, and/or a reduction in the enzymatic activity of transketolase or transaldolase in the micro-organisms, all compared to that of non-genetically modified micro-organisms (i.e. micro-organisms that have not been genetically modified for reduced transketolase activity or reduced transaldolase activity).

The reduction in the expression can be determined by measuring the quantity of transcripts coding for transketolase or transaldolase protein(s), for example; e.g. by way of Northern Blot analysis or RT-PCR. A reduction preferably means a reduction in the quantity of transcripts of at least 50%, preferably at least 70%, more preferably at least 85%, and most preferably at least 90% or even 100% (i.e. deletion or knock-out of expression) in comparison to corresponding micro-organisms that have not been genetically modified.

The reduction in the amount of transketolase or transaldolase protein, which results in a reduced transketolase or transaldolase activity can, for example, be determined by immunological methods such as Western blot analysis, ELISA (Enzyme Linked Immuno Sorbent Assay) or RIA (Radio Immune Assay). Here, a reduction preferably means a reduction in the amount of transketolase or transaldolase protein in comparison with corresponding micro-organisms that have not been genetically modified by at least 50%, in particular by at least 70%, preferably by at least 85% and particularly preferably by at least 90%.

In particular embodiments, the elimination of a certain enzymatic activity, such as the elimination of transketolase activity and/or the elimination of transaldolase activity, is achieved by deleting the endogenous gene(s) encoding the respective enzyme, such as the endogenous gene(s) encoding a transketolase and/or the endogenous gene(s) encoding a transaldolase.

In further embodiments, the micro-organisms described herein are further engineered to facilitate a metabolic pathway that allows for stoichiometric conversion of a carbon source to acetyl phosphate such as the conversion of 1 molecule fructose-6-phosphate into 3 molecules acetyl-phosphate, more particularly the conversion of 1 molecule fructose-6-phosphate and 2 molecules phosphate into 3 molecules acetyl-phosphate and 2 molecules water. Non-limiting examples of such metabolic pathways are the SPANOG pathway, the sedoheptulose phosphoketolase-assisted methanol condensation cycle (SPAMCC) and the GATHCYC pathway as described above. To facilitate these metabolic pathways, one or more competing pathways may be knocked out in the micro-organisms described herein, e.g. by deleting an enzyme of such a competing pathway, and/or the micro-organisms described herein may be further engineered to comprise the enzymes of these metabolic enzymes. Accordingly, in embodiments, the micro-organisms described herein may be further engineered to have eliminated activity of an enzyme of a competing pathway, e.g. an enzyme of a competing pathway may be deleted. In embodiments, the micro-organisms described herein may be further engineered to express or overexpress at least one of the enzymes of these metabolic pathways, i.e. one or more native enzymes of these metabolic pathways may be overexpressed, or one or more enzymes of these metabolic pathways may be introduced, or a combination of overexpression of one or more enzymes and introduction of one or more enzymes may be possible. In embodiments, the micro-organisms described herein may be further engineered to express or overexpress at least one of the enzymes of these metabolic pathways and to have eliminated activity of an enzyme of a competing pathway. In particular embodiments, the micro-organisms described herein are further engineered to have reduced or eliminated activity of an enzyme involved in (lower) glycolysis (e.g. PGK1 or a homolog thereof) and/or an enzyme of the pentose phosphate pathway (e.g. zwf1 or a homolog thereof). In particular embodiments, the micro-organisms described herein are further engineered to have reduced or eliminated activity of one or more of a phosphoglycerate kinase, a phosphofructokinase and a glucose-6-phosphate dehydrogenase. In further embodiments, the micro-organisms described herein are further engineered to have a deletion of at least one gene selected from a gene encoding a phosphoglycerate kinase (e.g. PGK1 or a homolog thereof), a gene encoding a phosphofructokinase (e.g. PFK or a homolog thereof) and a gene encoding a glucose-6-phosphate dehydrogenase (e.g. zwf1 or a homolog thereof).

In yet further embodiments, the micro-organisms described herein are further engineered to ensure the conversion of acetyl-phosphate into acetyl-CoA, which can further be converted to produce, for example, but without limitation, butanol, isobutanol, 2-pentanone and the like. Phosphate acetyltransferase (EC 2.3.1.8) is an enzyme that catalyzes the chemical reaction of acetyl-CoA+phosphate to CoA+acetyl phosphate and vice versa. Phosphate acetyltransferase is encoded in E. coli by pta. PTA is involved in conversion of acetate to acetyl-CoA. Specifically, PTA catalyzes the conversion of acetyl-CoA to acetyl-phosphate. PTA homologs and variants are well-known to the skilled person.

In certain embodiments, the micro-organisms are further engineered to ensure the production of a molecule of interest, said molecule of interest being derived from acetyl-CoA. For example, these further genetic modifications may encompass the expression or overexpression of one or more enzymes involved in the metabolic pathway for the production of the molecule of interest. Non-limiting examples of molecules of interest are acetone, isopropanol, butanol, isobutanol, isobutene, propene, polyketides, polyhydroxyalcanoates, hydroxyacids (including 3-hydroxypropionate, 3-hydrobutyrate, 3-hydroxyvalerate, 3-hydroxyhexanoate), fatty alcohols, fatty acids, all acetyl-coA derived natural amino acids (including glutamic acid, glutamine, aspartate, asparagine, proline, arginine, methionine, threonine, cysteine, succinate, lysine, leucine, isoleucine) and isoprenoids like farnesene. The yield of these molecules of interest is increased in the micro-organisms of the invention as compared to non-genetically modified micro-organisms that typically rely on pyruvate decarboxylation for acetyl phosphate generation.

Accordingly, the recombinant micro-organisms of the invention comprising an exogenous nucleic acid encoding an enzyme that ensures the irreversible conversion of sedoheptulose-7-phosphate, in particular a phosphoketolase having Spk activity, and having reduced transketolase activity and optionally having reduced transaldolase activity, can be distinguished in that they have higher yields for acetyl phosphate-derived molecules such as acetyl-CoA, and reduced $CO_2$ losses or in that these higher yields can be achieved at lower energetic and kinetic cost since there is no need for $CO_2$ re-fixation.

In particular embodiments, the micro-organisms can convert one or more sugar phosphate to acetyl phosphate. In a particular embodiment, the sugar phosphate is selected from the group consisting of: sugar phosphates of a triose (G3P, DHAP), an erythrose (E4P), a pentose (R5P, Ru5P, RuBP, X5P), a hexose (F6P, H6P, FBP, G6P), and a sedoheptulose (S7P, SBP), preferably a hexose, more preferably F6P.

The micro-organisms described herein can use various carbon sources to produce sugar phosphates. For example, the sugar phosphates may be derived from methanol, methane, CO2, CO, formaldehyde, formate, glycerol, a carbohydrate having the general formula CnH2nOn, wherein n=3 to 7, cellulose or hemicellulose as a carbon source. In particular embodiments, the micro-organisms are heterotrophic, mixotrophic, autotrophic or methanotrophic micro-organisms. The term "heterotrophic" as used herein in connection to micro-organisms refers to micro-organisms, e.g. yeasts, *E. coli, Clostridium* species, which grow on carbon-containing substrates or utilize organic matter for their growth. "Autotrophic micro-organisms" as used herein refers to micro-organisms, e.g. algae, which have the capacity to grow autonomously by photosynthesis. "Mixotrophic organisms" as used herein refers to micro-organisms, e.g. *Clostridium* species, which are capable using both photosynthesis ($CO_2$) and organic matter (e.g. syngas (CO, $H_2$)) present for their growth. These mixotrophs can be cultured both in the presence of light and of organic matter. "Methanotrophic micro-organisms" as used herein refers to micro-organisms that metabolize methane as their source of carbon.

Micro-organisms that are particularly useful for being engineered to convert a carbon source, in particular methanol, to acetyl phosphate via a sedoheptulose phosphoketolase-assisted methanol condensation cycle (SPAMCC) as described herein are mixotrophic and methanotrophic microorganisms.

The micro-organisms provided herein can be of bacterial origin, fungal, in particular yeast, or algal origin. In principle, any species of micro-organism that can be suitably transformed with and/or genetically modified can be used in the context of the present invention. In particular embodiments, the micro-organisms of the present invention are genetically modified bacteria or genetically modified fungi, in particular yeasts, or genetically modified algae. In particular embodiments, the micro-organism is a bacterium, such as a *Clostridium* species, in particular *Clostridium acetobutylicum*, or *E. coli*; or the micro-organism is a yeast, such as *S. cerevisae*. The methods for generating the metabolically engineered micro-organisms described herein involve standard genetic modifications, for which well-established methods are available to the skilled person.

The invention thus also encompasses methods for the production of the micro-organisms provided herein, more particularly methods for producing a micro-organism having increased production of a molecule of interest derived from acetyl-CoA. More particularly, the methods for producing the micro-organisms of the invention comprise introducing into a micro-organism of interest, at least one exogenous nucleic acid encoding a phosphoketolase having sedoheptulose-7-phosphate phosphoketolase activity. Optionally, the methods may further comprise, selecting micro-organisms with increased sedoheptulose-7-phosphate phosphoketolase activity and/or selecting a micro-organism having increased production of said molecule of interest compared to micro-organisms which do not comprise the exogenous nucleic acid encoding a phosphoketolase.

Genetic engineering of the host organism or cell through introduction of an exogenous nucleic acid encoding an enzyme of interest is accomplished in one or more steps via the design and construction of appropriate vectors and transformation of the host with those vectors.

Electroporation and/or chemical (such as calcium chloride- or lithium acetate-based) transformation methods or *Agrobacterium tumefaciens*-mediated transformation methods as known in the art can be used.

In particular embodiments, the exogenous nucleic acid encoding an enzyme of interest comprises a coding sequence encoding the enzyme of interest placed under the transcriptional control of one or more promoters and one or more terminators, both of which are functional in the host organism or cell.

Promoter and terminator sequences may be native to the host organism or cell or exogenous to the host organism or cell. Useful promoter and terminator sequences include those that are highly identical (i.e. having an identities score of 90% or more, preferably 95% or more, most preferably 99% or more) in their functional portions compared to the functional portions of promoter and terminator sequences, respectively, that are native to the host organism or cell, particularly when the insertion of the exogenous nucleic acid is targeted at a specific site in the host genome. The use of native (to the host organism or cell) promoters and terminators, together with their respective upstream and downstream flanking regions, can permit the targeted integration of the exogenous nucleic acid into specific loci of the host genome.

It is possible for the different coding sequences encoding an enzyme of interest to be placed under the control of different types of promoters and/or terminators.

Numerous vectors are known to practitioners skilled in the art, and selection of an appropriate vector is a matter of choice. The vectors can either be cut with particular restriction enzymes or used as circular DNA.

The vectors taught herein preferably comprise (a combination of) an exogenous nucleic acid as described herein. In particular, a vector comprises (a combination of) the coding sequence of an enzyme of interest and associated promoter and terminator sequences. The vector may contain restriction sites of various types for linearization or fragmentation. Vectors may further contain a backbone portion (such as for propagation in *E. coli*) many of which are conveniently obtained from commercially available yeast or bacterial vectors. The vector preferably comprises one or more selection marker gene cassettes. A "selection marker gene" is one that encodes a protein needed for the survival and/or growth of the transformed cell in a selective culture medium. Typical selection marker genes encode proteins that (a) confer resistance to antibiotics or other toxins such as chloramphenicol, zeocin (sh ble gene from *Streptoalloteichus hindustanus*), genetecin, melibiase (MEL5), hygromycin (aminoglycoside antibiotic resistance gene from *E. coli*), ampicillin, tetracycline, or kanamycin (kanamycin resistance gene of Tn903), (b) complement auxotrophic deficiencies of the cell. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3-) cannot grow on media lacking uracil. Thus a functional URA3 gene can be used as a marker on a cell having a uracil deficiency, and successful transformants can be selected on a medium lacking uracil. Only cells transformed with the functional URA3 gene are able to synthesize uracil and grow on such medium. If the wild-type strain does not have a uracil deficiency (as is the case with *I. orientalis*, for example), an auxotrophic mutant having the deficiency must be made in order to use URA3 as a selection marker for the strain. Methods for accomplishing this are well known in the art. The selection marker cassette typically further includes a promoter and terminator sequence, operatively linked to the selection marker gene, and which are operable in the host.

Successful transformants can be selected for in known manner, by taking advantage of the attributes contributed by the marker gene, or by other characteristics (such as ability to grow on specific substrates, such as e.g. sedoheptulose) contributed by the inserted exogenous nucleic acids. Screening can also be performed by PCR or Southern analysis to confirm that the desired insertions, and optionally deletions have taken place, to confirm copy number and to identify the point of integration of coding sequences into the host genome. Activity of the enzyme encoded by the inserted coding sequence can be confirmed using known assay methods.

In particular embodiments, the methods further comprise genetically modifying the micro-organism to have reduced or eliminated transketolase activity and optionally reduced or eliminated transaldolase activity.

Transketolase activity and transaldolase activity in metabolically engineered micro-organisms described herein may be reduced by any method that results in reduced activity of the transketolase or the transaldolase in the micro-organism. This may be achieved e.g. by altering transketolase or transaldolase at the DNA, mRNA and/or protein levels. In embodiments, transketolase activity or transaldolase activity may be reduced or eliminated by targeting genomic genes encoding a transketolase or a transaldolase. For example, the endogenous transketolase- or transaldolase-encoding gene(s) may be altered by, without limitation, knocking-out one or more transketolase- or transaldolase-encoding genes; knocking-in a heterologous DNA to disrupt one or more transketolase- or transaldolase-encoding genes; inactivating mutations. The skilled person would understand that these approaches may be applied to the coding sequences, the promoter or other regulatory elements necessary for gene transcription. In other embodiments, transketolase activity or transaldolase activity may be reduced by reducing levels of transketolase mRNA transcripts or transaldolase mRNA transcripts by methods known in the art including, but not limited to, co-suppression, antisense expression, small hair pin (shRNA) expression, interfering RNA (RNAi) expression, double stranded (dsRNA) expression, inverted repeat dsRNA expression, micro interfering RNA (miRNA), simultaneous expression of sense and antisense sequences, or a combination thereof, targeting transketolase- or transaldolase-encoding genes.

A further aspect provides methods for obtaining a metabolically engineered micro-organism as described herein, which methods comprise transforming the micro-organism with at least one exogenous nucleic acid encoding an enzyme that irreversibly converts sedoheptulose-7-phosphate as taught herein, in particular a phosphoketolase having Spk activity. In particular embodiments, the methods may comprise the steps of:
a) transforming the micro-organism with at least one exogenous nucleic acid encoding an enzyme that ensures the irreversible conversion of sedoheptulose-7-phosphate, in particular a phosphoketolase having Spk activity, as taught herein;
b) optionally genetically modifying the micro-organism to have reduced or eliminated transketolase activity and optionally reduced or eliminated transaldolase activity; and
c) selecting a micro-organism capable of high yield production of acetyl phosphate.

As detailed above, further genetic modifications are also envisaged herein.

Depending on the envisaged use of the micro-organisms of the invention and the enzymes present in said micro-organism, one or more additional modifications can be envisaged as described above. Accordingly, in particular embodiments, the methods further comprise engineering the micro-organism to express or overexpress at least one enzyme selected from the group comprising an enzyme having fructose-6-phosphoketolase and/or xylulose phosphoketolase activity, a transaldolase, a ribose-5-phosphate isomerase, a ribulose phosphate epimerase, a triose phosphate isomerase, a fructose 1,6-bisphosphate aldolase, and a fructose 1,6-bisphosphatase, preferably a fructose 1,6-bisphosphatase. In particular embodiments, the methods further comprise engineering the micro-organism to express or overexpress at least one enzyme selected from the group comprising an enzyme having fructose-6-phosphoketolase and/or xylulose-5-phosphoketolase activity; a transaldolase; a ribose-5-phosphate isomerase; a ribulose-5-phosphate epimerase; a triose-phosphate isomerase; a fructose-1,6-bisphosphate aldolase or a sedoheptulose-1,7-bisphosphate aldolase; a fructose-1,6 bisphosphatase or a sedoheptulose-1,7-bisphosphatase; a hexulose-6-phosphate synthase; a hexulose-6-phosphate isomerase; and a methanol dehydrogenase; or wherein the micro-organism is further engineered to express or overexpress at least one enzyme selected from the group comprising an enzyme having fructose-6-phosphoketolase and/or xylulose-5-phosphoketolase activity; a transaldolase; a ribose-5-phosphate isomerase; a ribulose-5-phosphate epimerase; a triose-phosphate isomerase; a fructose-1,6-bisphosphate aldolase or a sedoheptulose-1,7-bisphosphate aldolase; a fructose-1,6 bisphosphatase or a sedoheptulose-1,7-bisphosphatase; a dihydroxyacetone synthase; a fructose-6-phosphate aldolase; and a methanol dehydrogenase. In particular embodiments, the methods further comprise engineering the micro-organism to express or overexpress at least one enzyme selected from the group comprising an enzyme having fructose-6-phosphoketolase and/or xylulose-5-phosphoketolase activity, a sedoheptulose-1,7-bisphosphate aldolase, a sedoheptulose-1,7-bisphosphatase, a ribose-5-phosphate isomerase, a ribulose-5-phosphate epimerase and a triose phosphate isomerase, preferably a sedoheptulose-1,7-bisphosphatase.

In particular embodiments, the methods may further comprise genetically engineering the micro-organism to express or overexpress one or more enzymes required for the production of the product of interest.

The micro-organisms described herein are thus particularly useful for the biosynthesis of acetyl-phosphate, acetyl-CoA and/or products derived therefrom. Accordingly, a further aspect relates to the use of the micro-organisms described herein for the production of a molecule of interest, said molecule of interest being derived from acetyl-CoA. Also disclosed herein are methods for the production of a molecule of interest, said methods comprising culturing a micro-organism as described herein in the presence of a suitable carbon source. Non-limiting examples of suitable carbon sources include methanol, methane, $CO_2$, CO, formaldehyde, formate, glycerol, a carbohydrate having the general formula $C_nH_{2n}O_n$, wherein n=3 to 7, cellulose and hemicellulose.

The present invention will now be further illustrated by means of the following non-limiting examples.

EXAMPLES

Example 1: Kinetic Simulation of the NOG Pathway in C. acetobutylicum

The kinetic parameters of *C. acetobutylicum* enzymes involved in the NOG pathway were measured experimentally or estimated from literature (Table 1) and compiled in a COPASI toolbox for kinetic simulations.

TABLE 1

*C. acetobutylicum* NOG enzymes kinetic parameters, measured experimentally or estimated from literature.

|  | Xpk | Fbp |  |
|---|---|---|---|
| Km (µmol/ml) | 6.4 | 0.063 |  |
| V (µmol/(ml*s)) | 0.00041 | 0.00029 |  |

|  | Tal | Tkt | Tkt' |
|---|---|---|---|
| Keq | 1.051 | 1.21 | 101 |
| Vf (µmol/(ml*s)) | 0.0053 | 0.0035 | 0.0035 |
| Vr (µmol/(ml*s)) | 0.0051 | 0.0029 | 0.00035 |
| Kma (µmol/ml) | 0.272 | 0.67 | 0.946 |
| Kmb (µmol/ml) | 0.786 | 0.235 | 0.67 |
| Kmp (µmol/ml) | 1.44 | 0.1 | 1.1 |
| Kmq (µmol/ml) | 0.362 | 0.15 | 0.1 |

|  | Tpi | Fba | Rpe | Rpi |
|---|---|---|---|---|
| Kms (µmol/ml) | 6.45 | 1.14 | 5.97 | 2.47 |
| Kmp (µmol/ml) | 5.25 | 2 | 7.7 | 5.7 |
| Kmq (µmol/ml) | — | 2.4 | — | — |
| Ki (µmol/ml) | 35.5 | — | — | — |
| Kip (µmol/ml) | — | 10 | — | — |
| Keq | — | 0.069 (µmol/ml) | 1.41 | 41 |
| Vf (µmol/(ml*s)) | 0.5 | 0.0033 | 0.017 | 0.012 |
| Vr (µmol/(ml*s)) | 11.8 | 0.048 | — | — |

Figure 5:
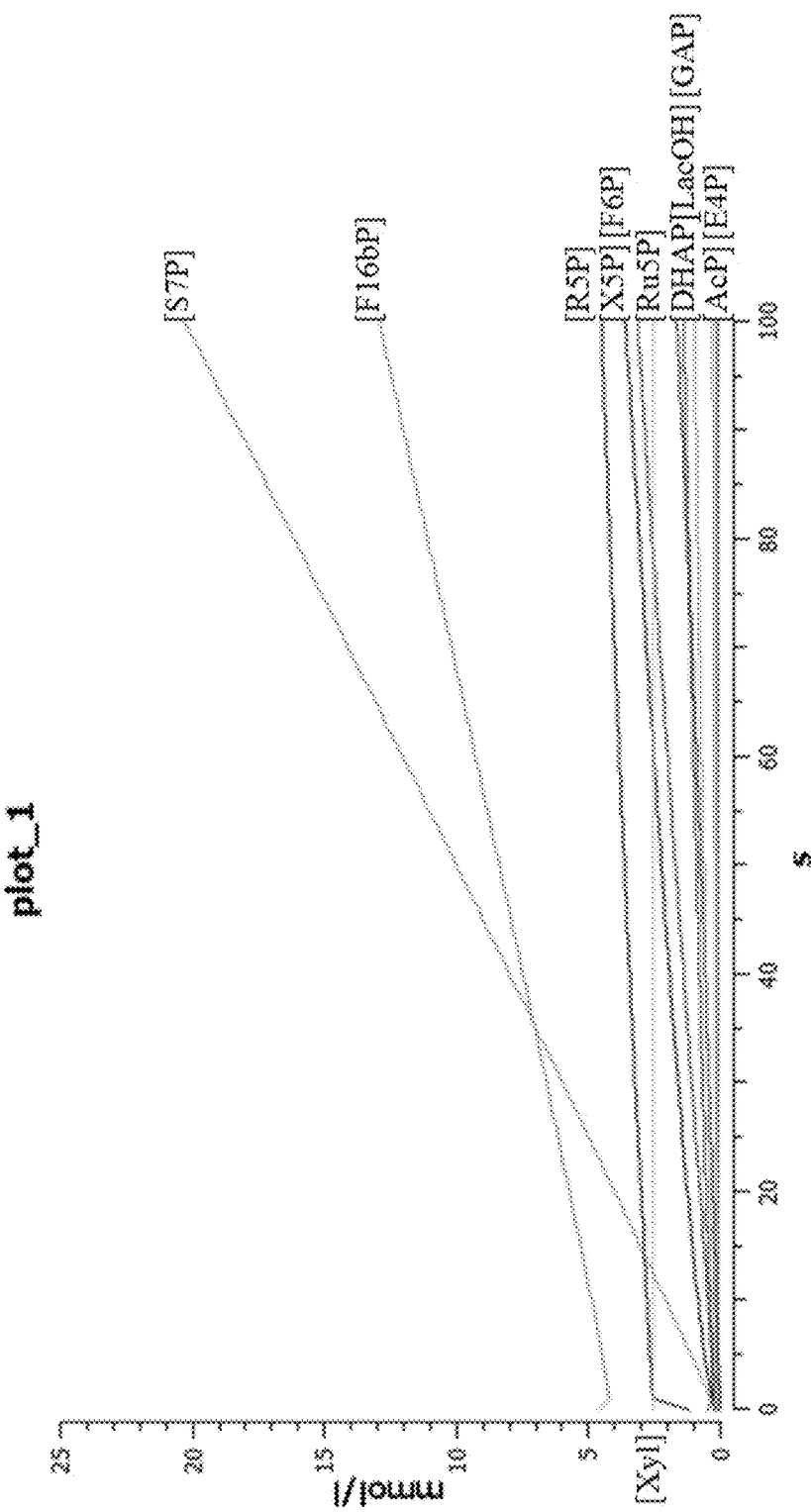
FIG. 5 shows a steady state simulation of the NOG pathway as illustrated in FIG. 1A with constant flux of xylose.

FIG. 5 shows a steady state simulation of the NOG pathway as illustrated in FIG. 1A with constant flux of xylose. FIG. 5 shows a rapid increase in S7P concentration (even faster than the product AcP). Such an increase in concentration would be lethal in vivo.

Figure 6:
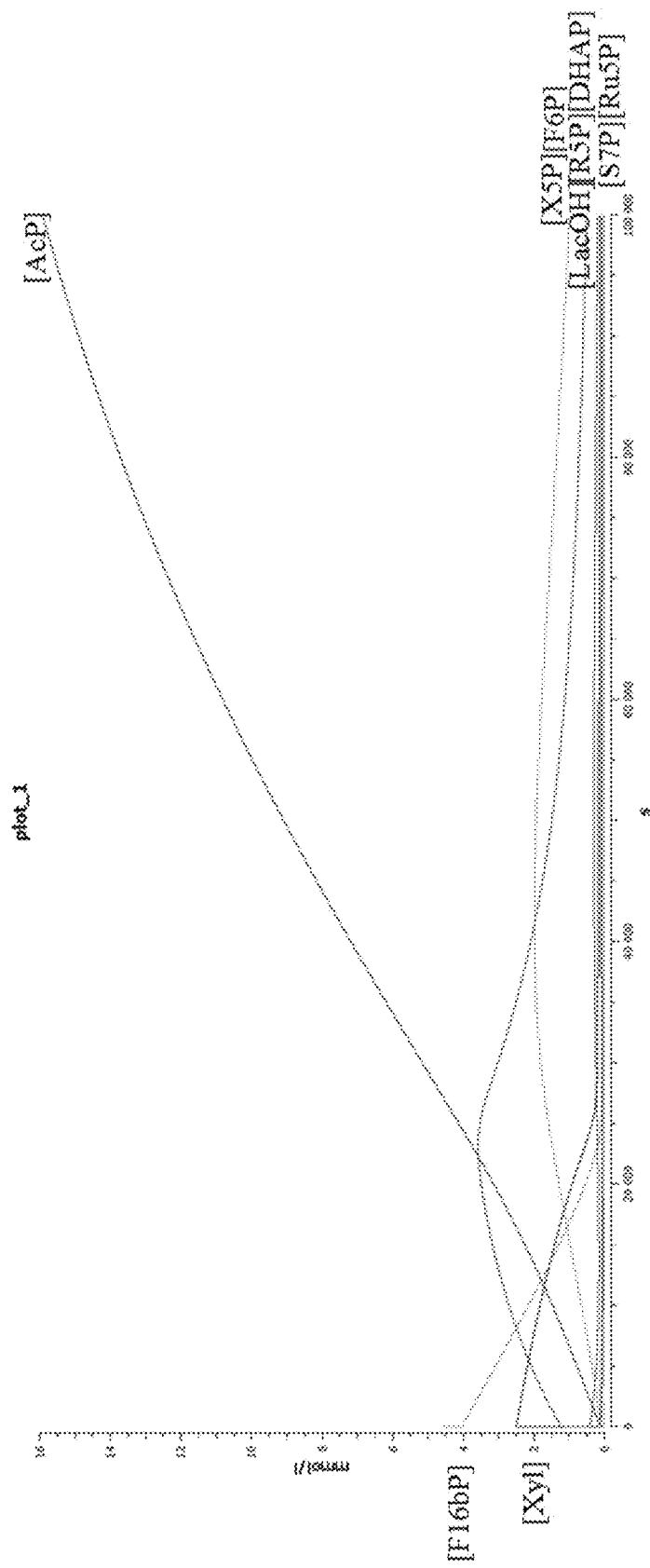
FIG. 6 shows a steady-state simulation of the SPANOG pathway as illustrated in FIG. 3D.

Following introduction of Spk (having the same kinetic parameters as the initial Xpk), the S7P accumulation was eliminated, the concentration of all metabolite intermediates reached a steady-state within in vivo tolerable concentrations and the accumulation of AcP was observed (FIG. 6).

Example 2: Identification of a Phosphoketolase Having Sedoheptulose-7-Phosphate Phosphoketolase Activity A yeast strain is constructed that has a deletion of the tkt gene(s) and the tal gene(s) and that expresses Fpk, Xpk or a bifunctional F/Xpk enzyme. Phosphoketolases are cloned into an expression plasmid and the yeast strain is transformed with these expression plasmids.

The yeast cells are grown on sedoheptulose and the transformants that survive are selected as containing a phosphoketolase having sedoheptulose-7-phosphate phosphoketolase activity.

Example 3: Identification and Characterization of a Phosphoketolase Having Sedoheptulose-7-Phosphate Phosphoketolase Activity Phosphoketolase activity of the phosphoketolases identified in Example 2 as having sedoheptulose-7-phosphate phosphoketolase activity is measured spectrophotometrically as ferric acetyl hydroxamate produced from the enzymatically generated acetyl phosphate by the procedure of Racker (1962 Methods Enzymol. 5:276-280). The standard reaction mixture of 0.075 ml consists of 33.3 mM potassium phosphate (pH 6.5), L-cysteine hydrochloride (1.9 mM), sodium fluoride (23 mM), sodium iodoacetate (8 mM), D-sedoheptulose-7-phosphate (Sigma) as a substrate (at a concentration of 27 mM), and finally the phosphoketolase-containing protein sample to initiate the reaction. After incubating at 37° C. for 30 min, 0.075 ml of hydroxylamine hydrochloride (2 M, pH 6.5) is added at room temperature. Ten minutes later, 0.05 ml of 15% (wt/vol) trichloroacetic acid, 0.05 ml of 4 M HCl, and 0.05 ml of FeCl3 z 6 H2O (5% [wt/vol] in 0.1 M HCl) are added for the final color development of the ferric hydroxamate, which is then spectrophotometrically quantified at 505 nm by comparing to a series of acetyl phosphate (Sigma) standards.

For qualitative measurements of S7PPK activity in whole cells, *E. coli* or other host cells containing recombinant phosphoketolase are pretreated with hexadecyltrimethylammonium bromide (Sigma) before being assayed according to the method of Orban and Patterson (2000 J. Microbiol. Methods 40:221-224).

One unit of phosphoketolase activity is defined as the amount of extract forming 1 µmol of acetyl phosphate per min from S7P. Specific activity is expressed as units per milligram of protein. Protein concentrations are determined by the method of Lowry et al. using bovine serum albumin as a standard.

Example 4: In Vivo Validation of the NOG Pathway in E. coli

The *E. coli* strains ΔldhA, ΔadhE, ΔmgsA, ΔfrdABCD, ΔpflAB, ΔpfkAB or ΔldhA, ΔadhE, ΔfrdBC, ΔpflB (*E. coli* strain JCL118 as described in Bogorad et al. (2013 Nature 502:693-698)) are further modified to have a deletion of the tkt and/or tal genes. The *E. coli* strains are transformed with the expression plasmid identified in Examples 2 and 3 as containing a phosphoketolase having sedoheptulose-7-phosphate phosphoketolase activity.

The *E. coli* cells are inoculated in growth medium containing a carbon source, e.g. a C6 sugar substrate, and incubated anaerobically to produce acetate. The final mixture is spin down, and a diluted supernatant is run on HPLC to measure carbon source and acetate concentration.

Example 5: In Vivo Validation of the SPANOG Pathway in Yeast (Saccharomyces cerevisiae)

A yeast strain, in particular the CEN.PK 113-5D yeast strain described in Bergman et al. (2016 AMB Express.

6(1):115), is further modified to reduce or eliminate 1) transketolase activity or 2) both transketolase and transaldolase activities. The yeast cells are further transformed with expression plasmids harboring phosphoketolase enzymes having sedoheptulose-7-phosphate phosphoketolase activity as identified in Examples 2 and 3 to monitor acetate production levels and growth rates on C6 sugar substrates as described in Example 4.

Example 6: In Vitro and In Vivo Validation of the SPANOG & GATHCYC Pathways in Yeast (*Saccharomyces cerevisiae*)

In order to evaluate whether the SPANOG or GATHCYC pathway is functional in yeast, yeast strains were constructed wherein all required enzymes are present (FIG. 8) and wherein competing pathways were knocked out. Acetyl phosphate (AcP) formation was measured in vitro in crude cell-free extracts using a phosphoketolase assay, and in vivo testing was performed by constructing strains that are dependent on a functional SPANOG or GATHCYC pathway to survive.

To enable the SPANOG pathway in yeast, in particular in *S. cerevisae*, the phosphoketolase Xfspk from *Bifidobacterium longum* was introduced, the native transketolases (TKL1, TKL2) were knocked out, and the native fructose-1,6-bisphosphatase (FBP1) and an cAMP insensitive fructose-1,6-bisphosphatase (glpX) from *E. coli* were over-expressed. In addition, PHO13 encoding for an alkaline phosphatase was deleted in the yeast strains to avoid formation of sedoheptulose via dephosphorylation of sedoheptulose-7-phosphate.

For the GATHCYC pathway, the phosphoketolase Xfspk from *B. longum* was introduced, the native transketolases (TKL1, TKL2) and the native transaldolases (TAL1, NQM1) were deleted, and the native sedoheptulose-1,7-bisphosphatase SHB17 was over-expressed. In addition, PHO13 was deleted in the yeast strains to avoid formation of sedoheptulose.

Pathway-negative strains were constructed as negative control. The pathway-negative strains had the same genotype as the pathway-positive strains, but the transaldolases (TAL1, NQM1) were deleted (tal1Δ nqm1Δ) for the SPANOG-negative strains, and sedoheptulose-1,7-bisphosphatase (SHB17) was deleted (shb17Δ) for GATHCYC-negative strain.

Figure 10:
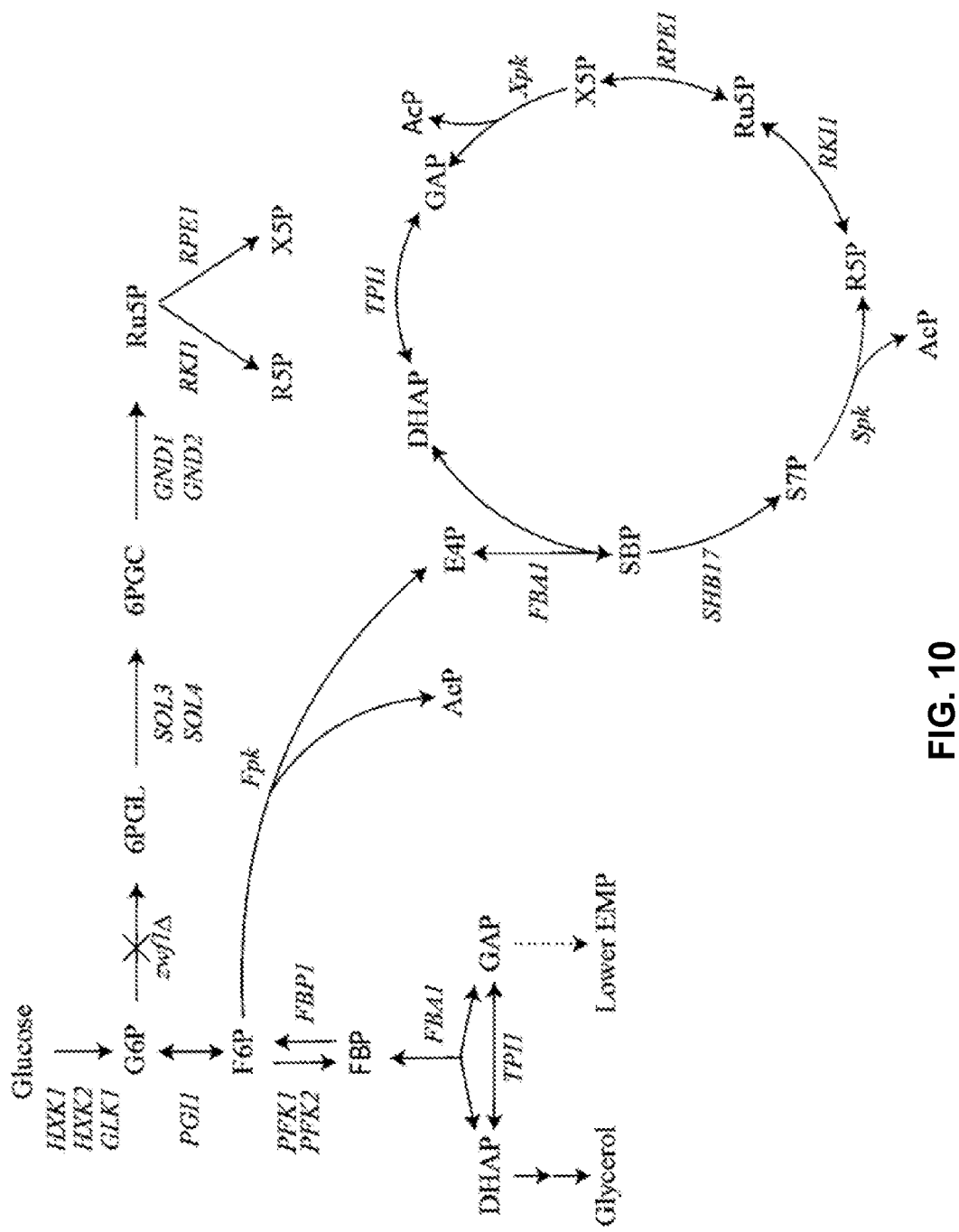
FIG. 10 shows upper glycolysis and the Pentose Phosphate pathway in a recombinant yeast, in particular S. cerevisae with GATHCYC background. The tkl1Δtkl2Δzwf1Δ background requires a functional GATH-CYC cycle to produce R5P from glucose.

Finally, the strains were further modified by deletion of the native ZWF1 gene to be dependent on a functional SPANOG or GATHCYC pathway to survive (FIG. 10). Indeed, knockout of both transketolases and the first step of the pentose phosphate (PP) pathway (ZWF1) has been reported to be lethal for *S. cerevisiae*, even when grown in the complex medium YPD, due to a lack of pentose phosphates (Schaaff-Gerstenschlager et al. 1993 Eur. J. Biochem. 217:487-492). Accordingly, only strains with a functional SPANOG OR GATHCYC cycle can produce R5P required for growth.

Materials and Methods

*Saccharomyces cerevisiae* Strains

The strains used are shown in Table 2. IMX581 (based on *Saccharomyces cerevisiae* CEN.PK113-5D, Mans et al. 2015 *FEMS Yeast Res.* 15:1-15) was used as a parental strain to construct the background required for testing the GATHCYC pathway. The pathway-negative strains have SHB17 deleted, which blocks the utilization of the full GATHCYC cycle.

TABLE 2

*Saccharomyces cerevisiae* strains used.

| Strain | Genotype | Notes |
|---|---|---|
| IMX581 | MATa ura3-52 can1Δ::cas9-natNT2 TRP1 LEU2 HIS3 | Cas9 expressing |
| JH1 | IMX581 tkl1/2Δ | |
| JH2 | JH1 tal1Δ nqm1Δ | |
| JH3 | JH2 pho13Δ shb14Δ | |
| JH4 | JH2 pho13Δ P$_{SHB17}$Δ::P$_{TDH3}$ | |
| JH9 | JH4 pJGH1 | Pathway positive |
| JH10 | JH3 pJGH1 | Pathway negative |
| JH18 | JH4 XII-1::xfspk cassette | Pathway positive |
| JH19 | JH3 XII-1::xfspk cassette | Pathway negative |
| JH20 | JH18 zwf1Δ | Pathway positive |

Cultivation Media

All chemicals were purchased from Sigma-Aldrich/Merck, unless otherwise specified. The growth medium for yeast strain construction was yeast-peptone-dextrose (YPD), containing 10 g/L yeast extract, 20 g/L peptone from meat and 20 g/L glucose. *E. coli* DH5a was used for plasmid construction and grown in lysogeny broth (LB), composed of 5 g/L yeast extract, 10 g/L peptone from casein and 10 g/L NaCl. Agar-agar was added at 20 g/L and 16 g/L to make YPD and LB plates, respectively.

*E. coli* transformants were selected on LB plates supplemented with 100 μg/mL ampicillin. Selection of yeast transformants was performed on synthetic complete dropout (SD) plates without uracil, which contained 6.9 g/L yeast nitrogen base (YNB) without amino acids (Formedium), 0.77 g/L complete supplement mix (CSM) without uracil (Formedium), 20 g/L glucose and 20 g/L agar-agar. 5-fluoroorotic acid (5-FOA) plates (containing 6.9 g/L YNB without amino acids, 0.77 g/L CSM, 1 g/L 5-FOA (Formedium), 20 g/L glucose and 20 g/L agar-agar) were used to remove the URA3 marker.

Cultivations prior phosphoketolase assay was performed in minimal medium, which contained 7.5 g/L $(NH_4)_2SO_4$, 14.4 g/L $KH_2PO_4$, 0.5 g/L $MgSO_4 \cdot 7H_2O$, 20 g/L glucose, 1 mL/L vitamin solution, 2 mL/L trace metal solution and pH set to 6.5. The vitamin solution and trace metal solution were prepared according to Verduyn et al. (1992 Yeast 8:501-517).

Strain and Plasmid Construction

Genomic modifications of *S. cerevisiae* IMX581 (strain CEN.PK113-5D constitutively expressing Cas9 from the genome) was performed by introducing a guide-RNA (gRNA) expressing plasmid according to workflow by Mans et al. (2015). *E. coli* transformations were performed according to Inoue et al. (1990 Gene 96:23-28). Table 3 shows the plasmids used for the GATHCYC configuration. The plasmid pJGH1 contains the promiscuous phosphoketolase gene from *Bifidobacterium longum* NCC2705 (SEQ ID NO: 3).

TABLE 3

Plasmids used for the GATHCYC configuration.

| Plasmid | Description | Origin |
|---|---|---|
| pMEL10-can1 | 2-n11origin ampR KlURA3 gRNA-CAN1.Y | Mans et al. (2015) |
| pROS10-can1/ade2 | 2-n1/ade2_ClampR URA3 gRNA-CAN1.Y gRNA-ADE2.Y | Mans et al. (2015) |
| pROS10-tkl1/tkl2 | pROS10 gRNA-TKL1 gRNA-TKL2 | Example 5 |
| pROS10-tal1/nqm1 | pROS10 gRNA-TAL1 gRNA-NQM1 | Example 5 |
| pROS10-pho13/shb17 | pROS10 gRNA-PHO13 gRNA-SHB17 | Example 5 |
| pROS10-pho13/shb17p | pROS10 gRNA-PHO13 gRNA-$P_{SHB17}$ | Example 5 |
| pMEL10-zwf1 | pMEL10 gRNA-ZWF1 | Example 5 |
| pQC032 | pROS10 gRNA-XII-1 integration site | Example 5 |
| pBS01A | 2-S01Arigin ampR URA3 pUC origin $P_{TEF1}$ - $P_{PGK1}$ | Example 5 |
| pJGH1 | pBS01A $P_{TEF1}$-Exfspk (*B. longum*) -$T_{ADH1}$ | Example 5 |

All kits, enzymes and buffers were ordered from Thermo Fisher Scientific, unless otherwise specified. The gRNA sequences were designed with the online tool Benchling and are listed in Table 4. PCR was performed with Phusion High-Fidelity DNA Polymerase and products purified using either GeneJET Gel Extraction or PCR Purification Kit. Primers were ordered from Eurofins Genomics.

plates were cultivated in YPD overnight and cryopreserved at −80° C. in 15% sterile glycerol, using a CoolCell container to maintain viability during freezing.

The gene coding for the phosphoketolase from *Bifidobacterium longum* NCC2705 (GenBank: AAN24771.1) was codon optimized for *S. cerevisiae* by Genscript (FIG. 9, SEQ ID NO: 3). The codon optimized xfspk (*B. longum*) was

TABLE 4 gRNA sequences used. Specificity score from Hsu et al.
(2013 Nat Biotechnol. 31:827-832) and efficiency
score from Doench, Fusi et al.
(2016 Nat Biotechnol. 34:184-191). The scores
are 0-100, higher is better.

| | Sequence | SEQ ID NO: | PAM | Specificity Score | Efficiency Score |
|---|---|---|---|---|---|
| gRNA-TKL1 | GCCAACTACAAACCATACGG | 4 | TGG | 99.6 | 76.3 |
| gRNA-TKL2 | CTTTGCCGCCACTTATAACG | 5 | AGG | 100.0 | 72.5 |
| gRNA-TAL1 | CTAGAACAATTGAAAGCCTC | 6 | CGG | 100.0 | 61.5 |
| gRNA-NQM1 | TGATCAAGATAGCTTCTACG | 7 | TGG | 100.0 | 71.5 |
| gRNA-SHB17 | GCAAAGAGCTAAGATCCGTG | 8 | TGG | 100.0 | 74.0 |
| gRNA-$P_{SHB17}$ | ACATTTTGTTCATAGCTAAG | 9 | TGG | 100.0 | 59.7 |
| gRNA-PHO13 | ACTGCAGTGTAACAGCCAAA | 10 | CGG | 99.4 | 61.6 |
| gRNA-ZWF1 | CCAGATAGAAGAGACGGTGT | 11 | GGG | 100.0 | 71.9 |

Single and double genomic modifications were performed by cloning the gRNAs into pMEL10 and pROS10, respectively, using Gibson assembly (NEB). The assembled plasmid was transformed to *E. coli*, extracted with GeneJET Plasmid Miniprep Kit and verified by Sanger sequencing (Eurofins Genomics). Transformation into yeast was performed with the lithium acetate/PEG method.

Repair fragments for gene deletions were ordered as two complementary 120 bp oligos (60 bp upstream and 60 bp downstream of the gene) and annealed before transformation. Fusion PCR was used to construct repair fragments for promoter replacement and cassette integration. Transformants were verified through colony PCR and sequencing. The URA3-based plasmid was recycled from successful transformants by plating on 5-FOA plates, and loss of plasmid confirmed by plating single colonies on both YPD and SD-ura plates. Clones that did not grow on SD-ura plates were cultivated in YPD overnight and cryopreserved at −80° C. in 15% sterile glycerol, using a CoolCell container to maintain viability during freezing.

The gene coding for the phosphoketolase from *Bifidobacterium longum* NCC2705 (GenBank: AAN24771.1) was codon optimized for *S. cerevisiae* by Genscript (FIG. 9, SEQ ID NO: 3). The codon optimized xfspk (*B. longum*) was cloned into pBS01A by restriction cloning with BcuI and NotI, placing it downstream of the TEF1 promoter.

Phosphoketolase Assay

The pathway was tested using purified crude cell free extracts. Briefly, single colonies of JH9 and JH10 were used to inoculate 2 mL minimal medium, using biological triplicates, and cultivated at 30° C. for 3 days at 200 rpm. The precultures were added to 100 mL unbaffled shake flasks containing 20 mL medium and cultivated 30° C. (200 rpm orbital shaking) until $OD_{600}$=1. The cells were washed once with 10 mL MQ water and once with 10 mL protein extraction buffer (PEB), containing 50 mM potassium phosphate buffer, 1 mM dithiothreitol, 2 mM MgSO4 and set to pH=7.5. The cells were resuspended in 0.4 mL PEB and snap frozen in liquid N2 after removal of supernatant. The cell pellet was stored at −80° C. until lysis.

Cells were thawed on ice prior lysis, resuspended in 0.4 mL PEB and transferred to a 2 mL screw-cap tube containing 500 mg 425-600 μm glass beads (Sigma G-8772). Halt protease inhibitor cocktail (Thermo Fisher Scientific) was added to a final concentration of 1×. The cells were homogenized with Precellys Evolution, using 4 cycles of 6800 rpm for 20 seconds, and kept on ice for 5 minutes between the cycles. Homogenate was transferred to an Eppendorf tube and cell debris spun down at 20 000 g for 10 min at 0° C. The supernatant was moved to a fresh tube and stored on ice. Harvesting and lysis procedures were performed on ice with cold solutions. The lysis and assay were performed on the same day.

The protein concentration of the crude cell-free extracts was determined in duplicates with DC protein assay kit (Bio-Rad), using premade BSA standards (Thermo Fisher Scientific). The samples were diluted to the same protein concentration with PEB. Production of acetyl phosphate evaluated with the ferric acetyl hydroxamate method, according to protocol modified from Bergman et al. (2016 AMB Express 6:115). Briefly, the assay was performed in a 96-well microplate, using a reaction volume of 75 μL consisting of 50 mM potassium phosphate buffer (pH 7.5), 1 mM $MgSO_4$, 8 mM iodoacetate, 23 mM NaF, 90 mM F6P and crude cell free extract. Reactions with lithium acetyl phosphate standards (0-16 mM) was performed in the same reaction buffer, but without F6P and crude cell free extract. The reaction was started by the addition of the crude cell free extract, and microplate was incubated at room temperature for 2 h. The reaction was stopped, and the product converted to ferric acetyl hydroxamate, using the same procedure as in Bergman et al. (2016), with the addition that the protein precipitate was removed by centrifuging the plate for 5 minutes at 2300 g. The supernatant was transferred to an empty plate and absorbance measured at 505 nm with the microplate reader FLUOstar® Omega (BMG Labtech GmbH, Ortenberg, Germany).

Results

Figure 11:
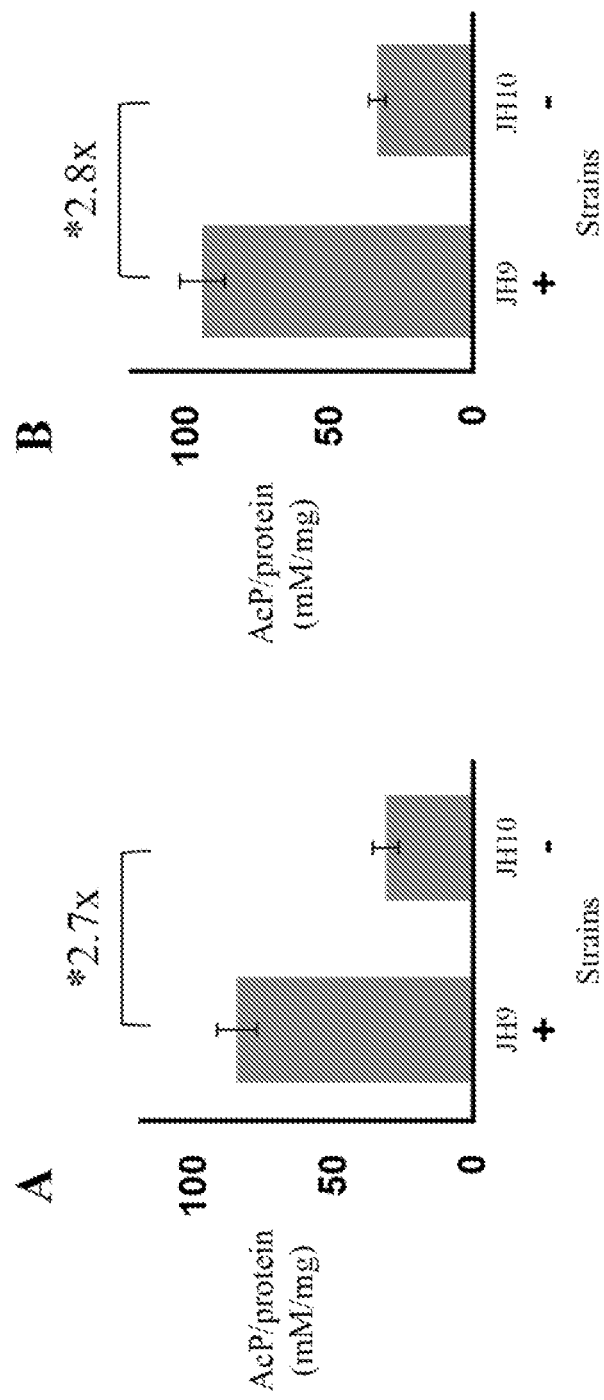
FIG. 11 shows the results of the in vitro testing of the GATHCYC pathway in the yeast S. cerevisae. An in vitro phosphoketolase assay was performed on crude cell-free extracts, with 90 mM fructose-6-phosphate (F6P) as substrate, for 2 h at room temperature. Both strains had the GATHCYC genotype, but JH10 was also shb17Δ so that full utilization of the GATHCYC cycle was blocked (pathway-negative). A) First trial with 130 µg total protein in all wells resulted in a final AcP concentration of 10.9 mM for JH9 (pathway-positive) and 4.0 mM for JH10 (pathway-negative). B) Second trial with 170 µg total protein resulted in a final AcP concentration of 15.7 mM for JH9 and 5.6 mM for JH10. Strains were grown in biological triplicates (except for the second trial, where JH9 used biological duplicates) and assayed in technical duplicates. Asterisks (*) indicate a significant difference ($p<0.001$, two-sided student's t-test with equal variance).

The results from the in vitro assay for the GATHCYC strains are shown in FIG. 11, wherein the strains express the phosphoketolase of *B. longum* on a high copy plasmid. The assay was performed twice, where the pathway-positive strains (JH9) yielded a 2.7 times higher signal compared to the pathway-negative control (JH10 strain) the first time (FIG. 11A) and 2.8 times higher the second time (FIG. 11B), indicating that the GATHCYC pathway is working in *S. cerevisae*.

Figure 12:
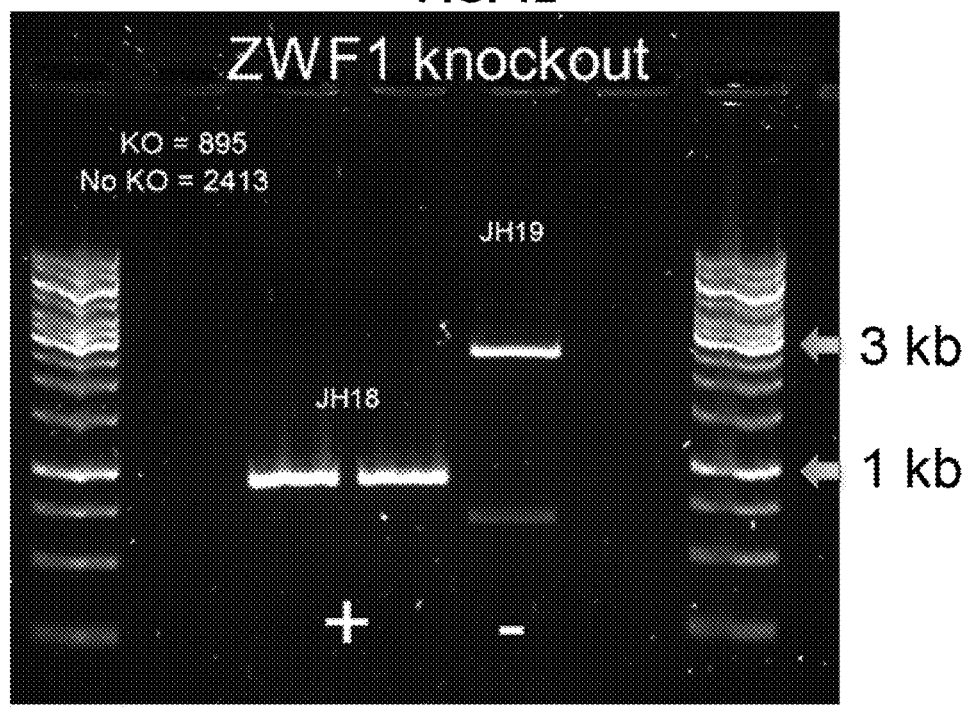
FIG. 12 shows the results of a colony PCR of JH18 and JH19 colonies. A ZWF1 knockout genotype resulted in an 895 bp band, whereas an intact ZWF1 showed a 2413 bp band.

In vivo activity of the GATHCYC pathway was demonstrated by deleting ZWF1 in the GATHCYC strains with genomic integration of the phosphoketolase (JH18 and JH19 strains) so that said strains are dependent on a functional GATHCYC pathway to survive, as this route will be the only way to produce RSP. Deleting ZWF1 in the pathway-negative strain (JH19 strain) was expected to be lethal. The transformation yielded ~50 sizeable colonies for JH18 (pathway positive) after 11 days and JH19 (pathway negative) yielded 1 colony after 3 days. However, colony PCR revealed that the ZWF1 was still intact in JH19 indicating that the colony was a false positive, whereas it was deleted in JH18 (FIG. 12). The PCR product of JH18 was confirmed by sequencing, and its GATHCYC background verified by PCR and sequencing of the fragments.

The combined results from the in vitro and in vivo experiment show that the GATHCYC pathway is functional in *S. cerevisae*.

Example 6: Acetate Production in *E. coli* Using the GATHCYC Pathway

The GATHCYC pathway is installed in *E. coli* PHL13 (Lin et al. 2018 Proc. Natl. Acad. Sci. U.S.A; 115/3538-3546). The phosphoketolase Xfspk from *B. longum* ($xfspk_{BL}$) and the sedoheptulose-1,7-bisphosphatase from *S. cerevisae* ($SHB17_{SC}$) are overexpressed from an operon containing $xfspk_{BL}$ and $SHB17_{SC}$), which are integrated into the genome, using CRISPR, under the control of the constitutive promoter miniPtac. The sedoheptulose 1,7-bisphosphate aldolase reaction is performed by the native fbaA. The native transketolases (tktA and tktB) and transaldolases (talA and talB) are deleted. The strains needed are shown in Table 5.

TABLE 5

*Escherichia coli* strains

| Strain | Genotype | Origin |
|---|---|---|
| PHL13 | BW25113/F'[traD36 proAB + laclqZΔM15 (Tetr)] ΔgapA::FRT ΔmgsA::FRT Δ(pgk gapB)::FRT ΔpfkA::FRT ΔiclR::FRT ΔpoxB::cat Δzwf::FRT RTedd eda)::($P_L$lacO1::xpkBA), PpckΔ::$P_L$lacO1 | Lin et al. (2018) |
| NOG21 | Evolved from PHL13 | Lin et al. (2018) |
| JHEC1 | PHL13 pCAS | Example 6 |
| JHEC2 | JHEC1 SS9::xfspk + shb17 cassette | Example 6 |
| JHEC3 | JHEC2 ΔtktA | Example 6 |
| JHEC4 | JHEC3 ΔtktB ΔtalA | Example 6 |
| JHEC5 | JHEC4 ΔtalB | Example 6 |
| JHEC6 | JHEC5 pJGHE3 | Example 6 |

The plasmids needed for strain construction are shown in Table 6. pJGHE3/4 can be chosen depending on the required expression of xfspk and SHB17.

TABLE 6

Plasmids for *E. coli* experiments

| Plasmid | Description | Origin |
|---|---|---|
| pCAS | repA101(Ts) kan $P_{cas}$-cas9 $P_{araB}$-Red laclq $P_{trc}$-sgRNA-pMB1 | Jiang et al. (2015 Appl. Environ. Microbiol. 81: 2506-2515) |
| pTargetF-cadA | pMB1 aadA sgRNA-cadA | Jiang et al. (2015) |
| pTargetT-SS9::xfspk + shb17 cassette | pTargetF sgRNA-SS9 | Example 6 |
| pTargetF-tktA | pTargetF sgRNA-tktA | Example 6 |
| pTargetF-talA | pTargetF sgRNA-talA | Example 6 |
| pTargetF-talB | pTargetF sgRNA-talB | Example 6 |
| pPL274 | $P_L$lacO1::xpkBA glfZM glk tkt2MB talKP glpX ColE ori Carbr | Lin et al. (2018) |
| pJGHE3 | PLlacO1::xfspkBL shb17SC glfZM glk ColE ori Carbr | Example 6 |
| pJGHE4 | PLlacO1::glfZM glk ColE ori Carbr | Example 6 |

The strain JHEC6 is evaluated for growth coupled acetate production and compared to NOG21, in a setup as described by Lin et al. (2018).

Example 7: 3-Hydroxy-Propionate (3-HP) Production in *S. cerevisiae* Using the GATHCYC Pathway The GATHCYC strain from Example 5 is further engineered for 3-HP production. GPP1 is deleted to avoid production of acetate from AcP, pta gene of *C. kluyveri* is introduced to convert AcP to acetyl-CoA and the mcr gene of *Chloroflexus auranticus* encoding malonyl-CoA reductase are introduced to produce 3-HP from malonyl-CoA. Furthermore, the copy number of xfspk from *B.*

*longum* is adjusted, as high-copy plasmid expression might be too high and genomic expression too low. A starting point is to increase the copy number by adding the xfspk on a centromeric plasmid to a strain with 1 copy of xfspk integrated into the genome. The strains are summarized in Table 7.

TABLE 7

Saccharomyces cerevisiae strains

| Strain | Genotype | Origin |
| --- | --- | --- |
| IMX581 | MATa ura3-52 can1Δ::cas9-natNT2 TRP1 LEU2 HIS3 | Mans et al. (2015) |
| JH4 | IMX581 tkl1/2Δ tal1Δ nqm1Δ pho13Δ P$_{SHB17}$Δ::P$_{TDH3}$ | Example 5 |
| JH24 | JH4 XII-1::xfspk cassette + P$_{PGK1}$-pta (*C. kluyveri*)-T$_{CYC1}$ | Example 7 |
| JH25 | JH24 gpp1Δ | Example 7 |
| JH26 | JH25 pJGH5 | Example 7 |
| JH27 | IMX581 XII-1::xfspk cassette + P$_{PGK1}$-pta (*C. kluyveri*)-T$_{CYC1}$ | Example 7 |
| JH28 | JH27 gpp1Δ | Example 7 |
| JH29 | JH28 pJGH5 | Example 7 |

The plasmids needed for the 3-HP production are shown in Table 8.

TABLE 8

Plasmids for *S. cerevisiae* experiments.

| Plasmid | Description | Origin |
| --- | --- | --- |
| P416TEF | centromeric URA3 ampR | Mumberg et al. (1995) |
| pJGH5 | p416TEF P$_{TEF1}$-Exfspk (*B. longum*) -T$_{ADH1}$ + P$_{TDH3}$-mcr-T$_{CYC1}$ | Example 7 |

Strain JH26 is evaluated in shake flasks and bioreactor, with JH29 as control. Both are characterized by determining the physiological parameters and through RNAseq and sugar phosphate analysis.

The invention claimed is:

1. A metabolically engineered micro-organism capable of increased acetyl phosphate conversion from a carbon source compared to a corresponding non-metabolically engineered micro-organism, wherein the micro-organism comprises at least one exogenous nucleic acid encoding a phosphoketolase having sedoheptulose-7-phosphate phosphoketolase activity, wherein the phosphoketolase having sedoheptulose-7-phosphate phosphoketolase activity is a *Bifidobacterium longum* phosphoketolase comprising the sequence set forth in SEQ ID NO: 2, and wherein the micro-organism is further genetically modified to have eliminated transketolase activity.

2. The micro-organism according to claim 1, wherein the micro-organism is genetically modified to have eliminated transaldolase activity.

3. The micro-organism according to claim 2, wherein the micro-organism is genetically modified to express or overexpress at least one enzyme selected from the group consisting of an enzyme having fructose-6-phosphoketolase and/or xylulose-5-phosphoketolase activity, a sedoheptulose-1,7-bisphosphate aldolase, a sedoheptulose-1,7-bisphosphatase, a ribose-5-phosphate isomerase, a ribulose-5-phosphate epimerase and a triose phosphate isomerase.

4. The micro-organism according to claim 3, wherein the micro-organism is genetically modified to express or overexpress a sedoheptulose-1,7-bisphosphatase.

5. The micro-organism according to claim 1, wherein the micro-organism is genetically modified to express or overexpress at least one enzyme selected from the group consisting of an enzyme having fructose-6-phosphoketolase and/or xylulose-5-phosphoketolase activity, a transaldolase, a ribose-5-phosphate isomerase, a ribulose-5-phosphate epimerase, a triose phosphate isomerase, a fructose 1,6-bisphosphate aldolase, and a fructose 1,6-bisphosphatase.

6. The micro-organism according to claim 5, wherein the micro-organism is genetically modified to express or overexpress a fructose-1,6-bisphosphatase.

7. The micro-organism according to claim 1, wherein the micro-organism is genetically modified to have reduced or eliminated activity of one or more of a phosphoglycerate kinase, a phosphofructokinase and a glucose-6-phosphate dehydrogenase.

8. The micro-organism according to claim 1, wherein the micro-organism is genetically modified to have reduced or eliminated activity of an alkaline phosphatase.

9. The micro-organism according to claim 1, wherein the micro-organism is further genetically modified to express or overexpress at least one enzyme of a pathway that converts acetyl-phosphate into a molecule of interest, said molecule of interest being selected from the group consisting of polyketides, polyhydroxyalcanoates, hydroxyacids, fatty alcohols, fatty acids, amino acids, acetone, isopropanol, butanol, isobutanol, isobutene, and propene.

10. The micro-organism according to claim 1, wherein the micro-organism is a bacterium or a yeast.

11. The micro-organism according to claim 10, wherein the microorganism is a yeast.

12. The micro-organism according to claim 1, wherein the micro-organism is *E. coli* or *S. cerevisae*.

13. The micro-organism according to claim 12, wherein the microorganism is *S. cerevisae*.

14. The micro-organism according to claim 1, wherein the phosphoketolase is encoded by a nucleic acid comprising the sequence set forth in SEQ ID NO: 3.

15. A method for the production of a molecule of interest, said molecule of interest being derived from acetyl-CoA and selected from the group consisting of polyketides, polyhydroxyalcanoates, hydroxyacids, fatty alcohols, fatty acids, amino acids, acetone, isopropanol, butanol, isobutanol, isobutene, and propene, wherein said method comprises:

culturing a metabolically engineered micro-organism according to claim 1 in the presence of a suitable carbon source that can be metabolized by said micro-organism.

* * * * *

SEQUENCE LISTING

<160> NUMBER OF SEQ ID NOS: 11

<210> SEQ ID NO 1
<211> LENGTH: 825
<212> TYPE: PRT
<213> ORGANISM: Bifidobacterium longum

<400> SEQUENCE: 1

Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
                20                  25                  30

Asn Tyr Leu Ser Ile Gly Gln Ile Tyr Leu Arg Ser Asn Pro Leu Met
            35                  40                  45

Lys Glu Pro Phe Thr Arg Glu Asp Val Lys His Arg Leu Val Gly His
        50                  55                  60

Trp Gly Thr Thr Pro Gly Leu Asn Phe Leu Ile Gly His Ile Asn Arg
65                  70                  75                  80

Phe Ile Ala Asp His Gly Gln Asn Thr Val Ile Ile Met Gly Pro Gly
                85                  90                  95

His Gly Gly Pro Ala Gly Thr Ser Gln Ser Tyr Leu Asp Gly Thr Tyr
            100                 105                 110

Thr Glu Thr Phe Pro Lys Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

```
Leu Pro Ile Leu His Leu Asn Gly Tyr Lys Ile Ala Asn Pro Thr Ile
    210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asp Glu Asp His
                245                 250                 255
Met Ser Ile His Arg Arg Phe Ala Glu Leu Trp Glu Thr Ile Trp Asp
            260                 265                 270
Glu Ile Cys Asp Ile Lys Ala Ala Gln Thr Asp Asn Val His Arg
        275                 280                 285
Pro Phe Tyr Pro Met Leu Ile Phe Arg Thr Pro Lys Gly Trp Thr Cys
290                 295                 300
Pro Lys Tyr Ile Asp Gly Lys Lys Thr Glu Gly Ser Trp Arg Ala His
305                 310                 315                 320
Gln Val Pro Leu Ala Ser Ala Arg Asp Thr Glu Ala His Phe Glu Val
                325                 330                 335
Leu Lys Asn Trp Leu Glu Ser Tyr Lys Pro Glu Glu Leu Phe Asp Ala
            340                 345                 350
Asn Gly Ala Val Lys Asp Val Leu Ala Phe Met Pro Lys Gly Glu
        355                 360                 365
Leu Arg Ile Gly Ala Asn Pro Asn Ala Asn Gly Gly Val Ile Arg Asp
    370                 375                 380
Asp Leu Lys Leu Pro Asn Leu Glu Asp Tyr Glu Val Lys Glu Val Ala
385                 390                 395                 400
Glu Tyr Gly His Gly Trp Gly Gln Leu Glu Ala Thr Arg Arg Leu Gly
                405                 410                 415
Val Tyr Thr Arg Asp Ile Ile Lys Asn Asn Pro Arg Asp Phe Arg Ile
            420                 425                 430
Phe Gly Pro Asp Glu Thr Ala Ser Asn Arg Leu Gln Ala Ser Tyr Glu
    435                 440                 445
Val Thr Asn Lys Gln Trp Asp Ala Gly Tyr Ile Ser Asp Glu Val Asp
450                 455                 460
Glu His Met His Val Ser Gly Gln Val Val Glu Gln Leu Ser Glu His
465                 470                 475                 480
Gln Met Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ala Ser Met Asn Leu Leu Val Ser Ser His Val Trp
530                 535                 540
Arg Gln Asp His Asn Gly Phe Ser His Gln Asp Pro Gly Val Thr Ser
545                 550                 555                 560
Val Leu Leu Asn Lys Cys Phe His Asn Asp His Val Ile Gly Ile Tyr
                565                 570                 575
Phe Ala Thr Asp Ala Asn Met Leu Leu Ala Ile Ala Glu Lys Cys Tyr
            580                 585                 590
Lys Ser Thr Asn Lys Ile Asn Ala Ile Ala Gly Lys Gln Pro Ala
        595                 600                 605
Ala Thr Trp Leu Thr Leu Asp Glu Ala Arg Ala Glu Leu Glu Lys Gly
610                 615                 620
Ala Ala Ala Trp Asp Trp Ala Ser Thr Ala Lys Asn Asn Asp Glu Ala
```

```
            625                 630                 635                 640
    Glu Val Val Leu Ala Ala Gly Asp Val Pro Thr Gln Glu Ile Met
                        645                 650                 655

Ala Ala Ser Asp Lys Leu Lys Glu Leu Gly Val Lys Phe Lys Val Val
                        660                 665                 670

Asn Val Ala Asp Leu Leu Ser Leu Gln Ser Ala Lys Glu Asn Asp Glu
                        675                 680                 685

Ala Leu Thr Asp Glu Glu Phe Ala Asp Ile Phe Thr Ala Asp Lys Pro
                        690                 695                 700

Val Leu Phe Ala Tyr His Ser Tyr Ala His Asp Val Arg Gly Leu Ile
    705                 710                 715                 720

Tyr Asp Arg Pro Asn His Asp Asn Phe Asn Val His Gly Tyr Glu Glu
                        725                 730                 735

Glu Gly Ser Thr Thr Thr Pro Tyr Asp Met Val Arg Val Asn Arg Ile
                        740                 745                 750

Asp Arg Tyr Glu Leu Thr Ala Glu Ala Leu Arg Met Ile Asp Ala Asp
                        755                 760                 765

Lys Tyr Ala Asp Lys Ile Asp Glu Leu Glu Lys Phe Arg Asp Glu Ala
                        770                 775                 780

Phe Gln Phe Ala Val Asp Lys Gly Tyr Asp His Pro Asp Tyr Thr Asp
    785                 790                 795                 800

Trp Val Tyr Ser Gly Val Asn Thr Asp Lys Lys Gly Ala Val Thr Ala
                        805                 810                 815

Thr Ala Ala Thr Ala Gly Asp Asn Glu
                        820                 825

<210> SEQ ID NO 2
<211> LENGTH: 825
<212> TYPE: PRT
<213> ORGANISM: Bifidobacterium longum strainNCC 2705

<400> SEQUENCE: 2

Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
                20                  25                  30

Asn Tyr Leu Ser Ile Gly Gln Ile Tyr Leu Arg Ser Asn Pro Leu Met
            35                  40                  45

Lys Glu Pro Phe Thr Arg Glu Asp Val Lys His Arg Leu Val Gly His
        50                  55                  60

Trp Gly Thr Thr Pro Gly Leu Asn Phe Leu Ile Gly His Ile Asn Arg
65                  70                  75                  80

Phe Ile Ala Asp His Gly Gln Asn Thr Val Ile Met Gly Pro Gly
                85                  90                  95

His Gly Gly Pro Ala Gly Thr Ser Gln Ser Tyr Leu Asp Gly Thr Tyr
                100                 105                 110

Thr Glu Thr Phe Pro Lys Ile Thr Lys Asp Glu Ala Gly Leu Gln Lys
            115                 120                 125

Phe Phe Arg Gln Phe Ser Tyr Pro Gly Gly Ile Pro Ser His Phe Ala
        130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175
```

```
Pro Ala Ile Val Gly Asp Gly Glu Ala Glu Thr Gly Pro Leu Ala Thr
                180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asp Glu Asp His
                245                 250                 255

Met Ser Ile His Arg Arg Phe Ala Glu Leu Trp Glu Thr Ile Trp Asp
            260                 265                 270

Glu Ile Cys Asp Ile Lys Ala Thr Ala Gln Thr Asp Asn Val His Arg
        275                 280                 285

Pro Phe Tyr Pro Met Leu Ile Phe Arg Thr Pro Lys Gly Trp Thr Cys
    290                 295                 300

Pro Lys Tyr Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Asp Asp Val Leu Ala Phe Met Pro Lys Gly Glu
        355                 360                 365

Leu Arg Ile Gly Ala Asn Pro Asn Ala Asn Gly Gly Val Ile Arg Asn
    370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Thr Leu Gly
                405                 410                 415

Ala Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ala Ser Met Asn Leu Leu Val Ser Ser His Val Trp
530                 535                 540

Arg Gln Asp His Asn Gly Phe Ser His Gln Asp Pro Gly Val Thr Ser
                545                 550                 555                 560

Val Leu Leu Asn Lys Cys Phe His Asn Asp His Val Ile Gly Ile Tyr
            565                 570                 575

Phe Ala Thr Asp Ala Asn Met Leu Leu Ala Ile Ala Glu Lys Cys Tyr
        580                 585                 590

Lys Ser Thr Asn Lys Ile Asn Ala Ile Ile Ala Gly Lys Gln Pro Ala
```

```
             595                 600                 605
Ala Thr Trp Leu Thr Leu Asp Glu Ala Arg Ala Glu Leu Glu Lys Gly
        610                 615                 620

Ala Ala Ala Trp Asp Trp Ala Ser Thr Ala Lys Asn Asn Asp Glu Ala
625                 630                 635                 640

Glu Val Val Leu Ala Ala Gly Asp Val Pro Thr Gln Glu Ile Met
                645                 650                 655

Ala Ala Ser Asp Lys Leu Lys Glu Leu Gly Ile Lys Phe Lys Val Val
            660                 665                 670

Asn Val Ala Asp Leu Leu Ser Leu Gln Ser Ala Lys Glu Asn Asp Glu
            675                 680                 685

Ala Leu Thr Asp Glu Glu Phe Ala Asp Ile Phe Thr Ala Asp Lys Pro
        690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Arg Ile
            740                 745                 750

Asp Arg Tyr Glu Leu Thr Ala Glu Ala Leu Arg Met Ile Asp Ala Asp
            755                 760                 765

Lys Tyr Ala Asp Lys Ile Asp Glu Leu Glu Lys Phe Arg Asp Glu Ala
770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asp Lys Lys Gly Ala Val Thr Ala
                805                 810                 815

Thr Ala Ala Thr Ala Gly Asp Asn Glu
            820                 825

<210> SEQ ID NO 3
<211> LENGTH: 2478
<212> TYPE: DNA
<213> ORGANISM: Artificial Sequence
<220> FEATURE:
<223> OTHER INFORMATION: Phosphoketolase gene of Bifidobacterium longum
      strain NCC 2705 codon-opimized for S. cerevisae

<400> SEQUENCE: 3
atgacatccc ctgtaattgg tactccttgg aagaagttga acgccccagt ctcagaagaa      60
gcattggaag tgttgataa gtattggaga gttgcaaatt acttgtcaat ggtcaaattt     120
tacttgagat caaatccatt gatgaaagaa ccattcacta gagaagatgt taaacataga     180
ttggttggtc attggggtac aactccaggt ttaaatttct tgattggtca tattaataga     240
ttcattgctg atcatggtca aaatacagtt attattatgg gtccaggtca tggtggtcca     300
gctggtactt cacaatctta cttggatggt acttatacag aaactttttc caaaaattact     360 aaagatgaag caggtttgca aaaattttt cagacaattt tcttatccagg tggtattcca     420 tctcattttg caccagaaac accaggttca attcatgaag gtggtgaatt gggttacgct     480
ttgtctcatg cttatggtgc aattatggat aatccatctt gtttgttcc agctattgtt     540 ggtgacggtg aagctgaaac tggtccattg ctactggtt ggcaatcaaa taagttggtt     600
aatccaagaa ctgatggtat tgttttacca attttgcatt gaatggtta caaaattgct     660 aatccaacaa ttttatcaag aatttctgat gaagaattgc atgaattttt ccatggtatg     720
```

-continued

```
ggttacgaac catacgaatt tgttgcaggt tttgatgatg aagatcatat gtcaattcat      780
agaagatttg ctgaattatg ggaaacaatt tgggatgaaa tttgtgatat taaagcaaca      840
gctcaaactg ataatgttca tagaccattt tatccaatgt tgattttag aacaccaaaa       900 ggttggactt gtccaaaata tattgatggt aaaaagactg aaggttcatg gagatcacat      960
caagttccat tagcatctgc tagagatact gaagcacatt ttgaagtttt gaaaaattgg    1020
ttggaatctt ataaaccaga agaattgttt gatgcaaatg gtgcagttaa agatgatgtt    1080
ttagctttta tgccaaaagg tgaattgaga attggtgcta atccaaatgc taatggtggt    1140
gttattagaa atgatttgaa attaccaaat ttggaagatt acgaagttaa agaagttgca    1200
gaatacggtc atggttgggg tcaattggaa gctactagaa ctttaggtgc ttatactaga    1260
gatattatta aaataatcc aagagatttt agaattttg gtccagatga aactgcttct      1320
aatagattgc aagcatctta tgaagttact aataagcaat gggatgctgg ttatatttca    1380
gatgaagttg atgaacatat gcatgtttca ggtcaagttg ttgaacaatt gtcagaacat    1440
caaatggaag gtttcttgga agcatacttg ttaacaggta gacatggtat ttggtcatct    1500
tatgaatctt ttgttcatgt tattgattca atgttaaatc aacatgcaaa atggttggaa    1560
gctacagtta gagaaattcc atggagaaaa ccaattgcat ctatgaattt gttagtttct    1620
tcacatgttt ggagacaaga tcataatggt ttttcacatc aagatccagg tgttacttct    1680
gttttgttga ataagtgttt tcataatgat catgttattg gtatttactt tgcaactgat    1740
gctaatatgt tgttagctat tgctgaaaaa tgttacaaat caactaataa gattaatgca    1800
attattgctg gtaaacaacc agcagctact tggttaacat tggatgaagc tagagcagaa    1860
ttagaaaaag gtgcagctgc ttgggattgg gcatctactg ctaaaaataa tgatgaagct    1920
gaagttgttt tagcagcagc tggtgacgtt ccaactcaag aaattatggc agcttcagat    1980
aaattgaaag aattgggtat taaattcaaa gttgttaatg ttgcagattt gttatcattg    2040
caatctgcta agaaaatga tgaagcatta actgatgaag aatttgctga tatttttaca    2100
gctgataaac cagttttatt tgcttaccat tcttatgctc atgatgttag aggtttgatt    2160
tacgatagac caaatcatga taattttaat gttcatggtt atgaagaaga aggttcaact    2220
acaactccat acgatatggt tagagttaat agaattgata gatacgaatt gactgctgaa    2280
gcattgagaa tgattgatgc agataaatac gcagataaaa ttgatgaatt ggaaaaattc    2340
agagatgaag catttcaatt tgcagttgat aatggttatg atcatccaga ttatacagat    2400
tgggtttact caggtgtaaa taccgacaaa aagggtgctg taaccgctac cgctgctacc    2460
gctggtgaca acgaataa                                                  2478
```

<210> SEQ ID NO 4
<211> LENGTH: 20
<212> TYPE: DNA
<213> ORGANISM: Artificial Sequence
<220> FEATURE:
<223> OTHER INFORMATION: gRNA-TKL1

<400> SEQUENCE: 4

```
gccaactaca aaccatacgg                                                   20
```

<210> SEQ ID NO 5
<211> LENGTH: 20
<212> TYPE: DNA
<213> ORGANISM: Artificial Sequence
<220> FEATURE:
<223> OTHER INFORMATION: gRNA-TKL2

```
<400> SEQUENCE: 5
ctttgccgcc acttataacg                                          20

<210> SEQ ID NO 6
<211> LENGTH: 20
<212> TYPE: DNA
<213> ORGANISM: Artificial Sequence
<220> FEATURE:
<223> OTHER INFORMATION: gRNA-TAL1

<400> SEQUENCE: 6
ctagaacaat tgaaagcctc                                          20

<210> SEQ ID NO 7
<211> LENGTH: 20
<212> TYPE: DNA
<213> ORGANISM: Artificial Sequence
<220> FEATURE:
<223> OTHER INFORMATION: gRNA-NQM1

<400> SEQUENCE: 7
tgatcaagat agcttctacg                                          20

<210> SEQ ID NO 8
<211> LENGTH: 20
<212> TYPE: DNA
<213> ORGANISM: Artificial Sequence
<220> FEATURE:
<223> OTHER INFORMATION: gRNA-SHB17

<400> SEQUENCE: 8
gcaaagagct aagatccgtg                                          20

<210> SEQ ID NO 9
<211> LENGTH: 20
<212> TYPE: DNA
<213> ORGANISM: Artificial Sequence
<220> FEATURE:
<223> OTHER INFORMATION: gRNA- PSHB17

<400> SEQUENCE: 9
acattttgtt catagctaag                                          20

<210> SEQ ID NO 10
<211> LENGTH: 20
<212> TYPE: DNA
<213> ORGANISM: Artificial Sequence
<220> FEATURE:
<223> OTHER INFORMATION: gRNA- PHO13

<400> SEQUENCE: 10
actgcagtgt aacagccaaa                                          20

<210> SEQ ID NO 11
<211> LENGTH: 20
<212> TYPE: DNA
<213> ORGANISM: Artificial Sequence
<220> FEATURE:
<223> OTHER INFORMATION: gRNA- ZWF1

<400> SEQUENCE: 11
ccagatagaa gagacggtgt                                          20
```